(12) United States Patent
Knowlton

(10) Patent No.: US 6,427,089 B1
(45) Date of Patent: Jul. 30, 2002

(54) STOMACH TREATMENT APPARATUS AND METHOD

(76) Inventor: Edward W. Knowlton, 5478 Blackhawk Dr., Danville, CA (US) 94506

( * ) Notice: Subject to any disclaimer, the term of this patent is extended or adjusted under 35 U.S.C. 154(b) by 0 days.

(21) Appl. No.: 09/507,597
(22) Filed: Feb. 18, 2000

Related U.S. Application Data

(60) Provisional application No. 60/120,781, filed on Feb. 19, 1999.

(51) Int. Cl.$^7$ ................................................ A61F 2/00
(52) U.S. Cl. ......................... 607/101; 607/105; 607/113
(58) Field of Search ................. 606/27–29; 607/98–102, 607/105, 113, 116, 133, 138, 154, 156

(56) References Cited

U.S. PATENT DOCUMENTS

| | | | |
|---|---|---|---|
| 4,638,813 A | * 1/1987 | Turner | |
| 5,007,437 A | * 4/1991 | Sterzer | 428/786 |
| 5,057,106 A | 10/1991 | Kasevich et al. | 606/33 |
| 5,275,597 A | * 1/1994 | Higgins et al. | 606/33 |
| 5,496,271 A | 3/1996 | Burton et al. | 604/54 |
| 5,628,771 A | 5/1997 | Mizukawa et al. | 607/102 |
| 5,776,176 A | 7/1998 | Rudie | 607/101 |
| 6,002,968 A | * 12/1999 | Edwards | 606/41 |
| 6,056,744 A | * 5/2000 | Edwards | 606/41 |
| 6,073,052 A | * 6/2000 | Zelickson et al. | 607/100 |

FOREIGN PATENT DOCUMENTS

| | | | |
|---|---|---|---|
| EP | 0 105 677 | 4/1984 | A61N/5/04 |
| WO | WO 99/35988 | 7/1999 | A61B/17/39 |

* cited by examiner

Primary Examiner—Roy D. Gibson
(74) Attorney, Agent, or Firm—Paul Davis; Heller Ehrman White & McAuliffe

(57) ABSTRACT

An apparatus to modify a stomach wall comprises an elongated member including at least one lumen. A deployable member is coupled to the elongated member. The deployable member is configured to be advanceable and removable from the stomach in a non-deployed state and sized to be positioned in the stomach in a deployed state to engage at least portions of the stomach wall. The deployable member is further configured to house a fluidic media and at least portions of the deployable member wall is configured to be cooled by the fluidic media. The deployable member has a contour in the deployed state approximating at least a portion of a stomach. A microwave antenna is movably positioned in the deployable member so as to control a microwave field strength vector in relation to the antenna. The microwave antenna is configured to be coupled to a microwave energy source and deliver microwave energy to a selectable tissue site in the stomach wall while minimizing thermal injury to one of a mucosal or a submucosal layer. A cable member is coupled to the microwave antenna and is configured to be advanceable within the elongated member.

68 Claims, 12 Drawing Sheets

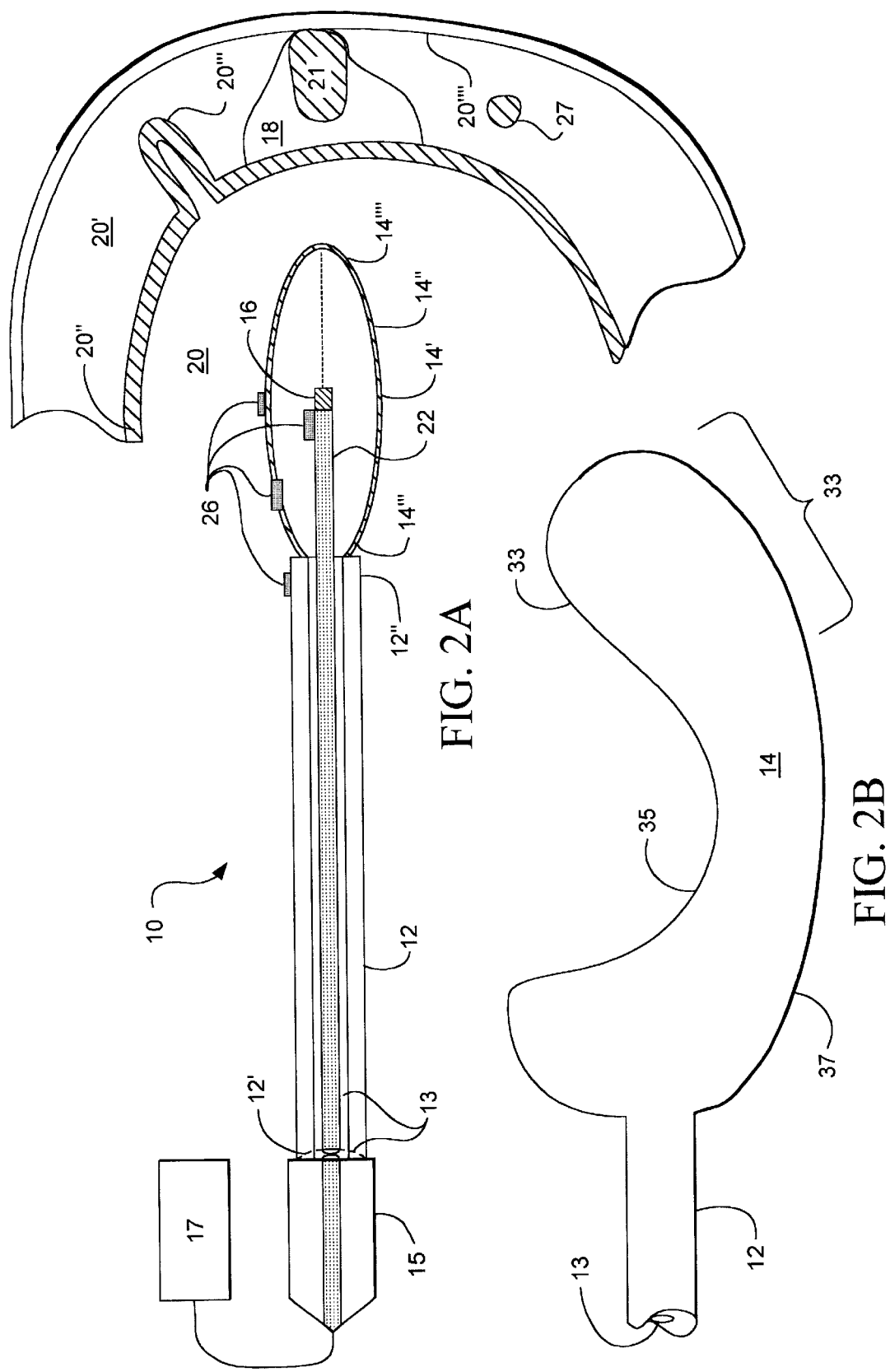

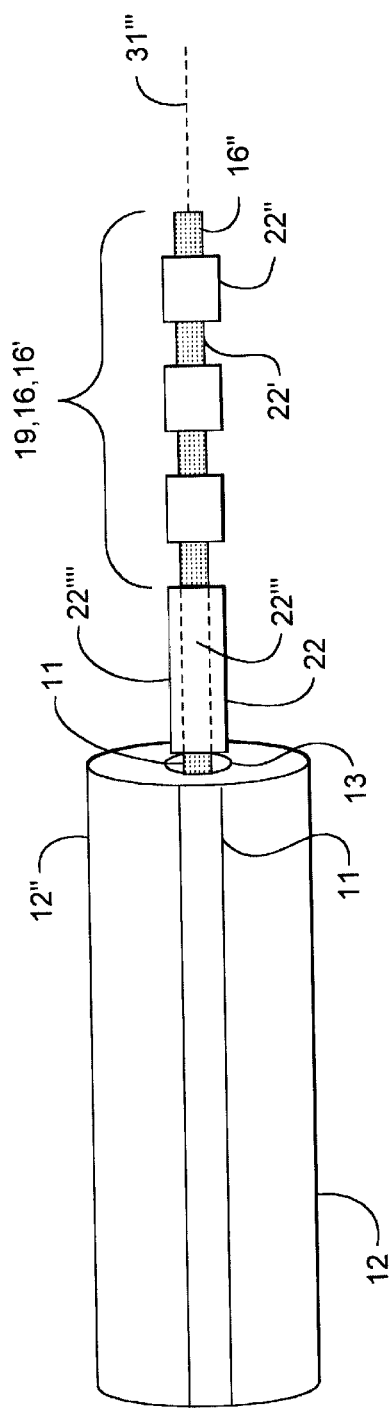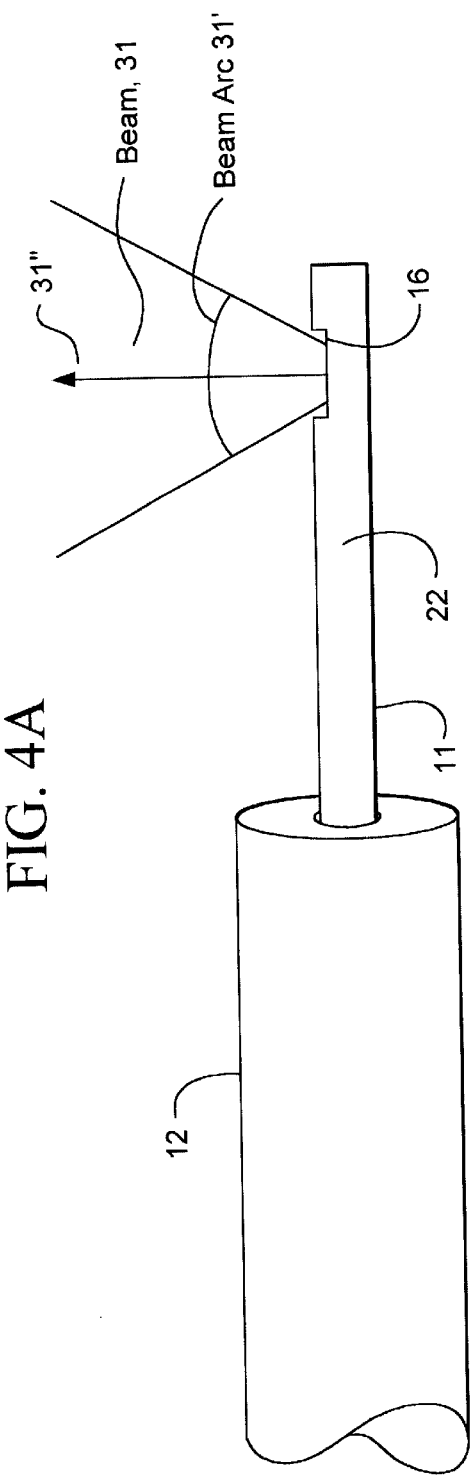
FIG. 4A
FIG. 4B

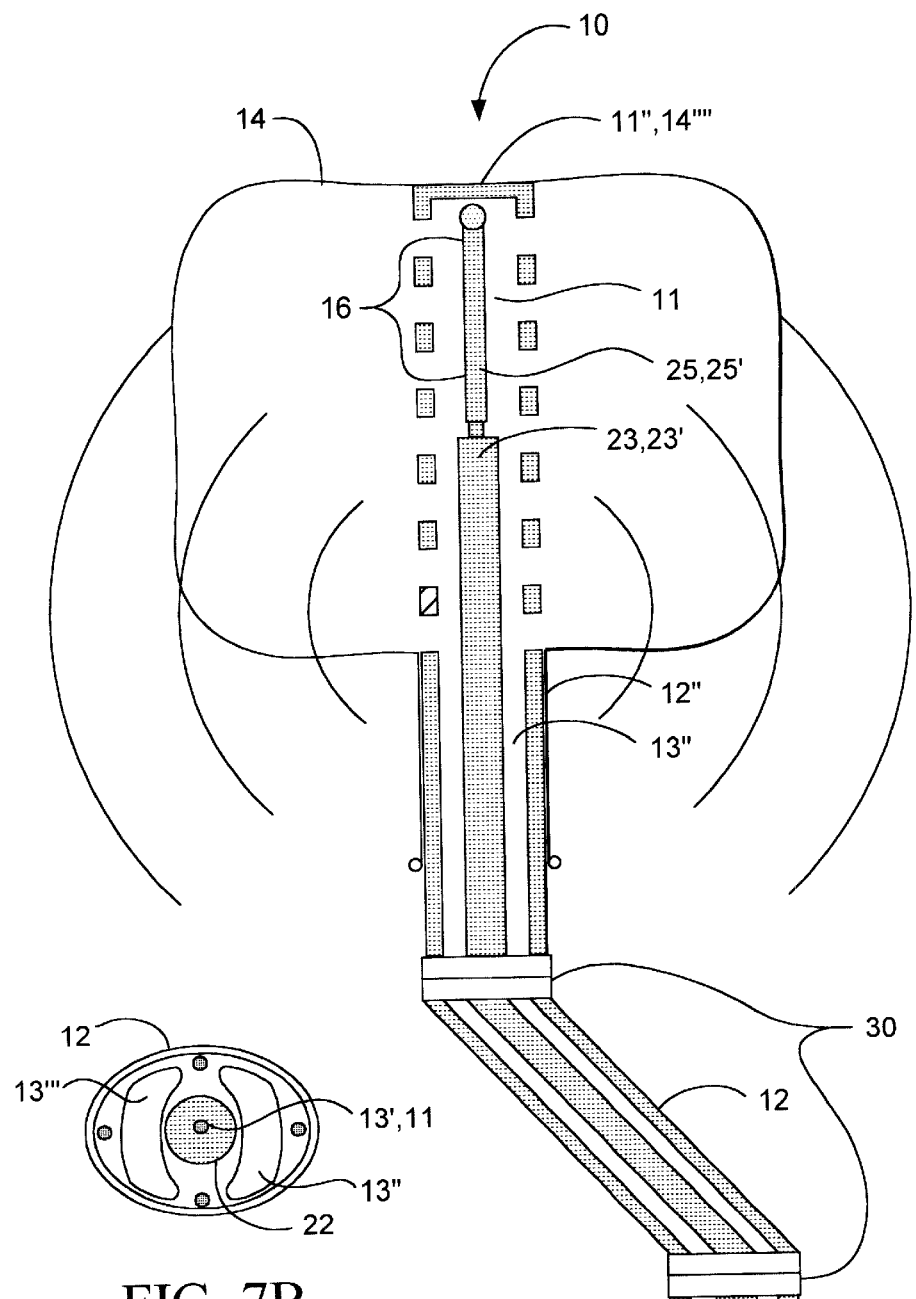
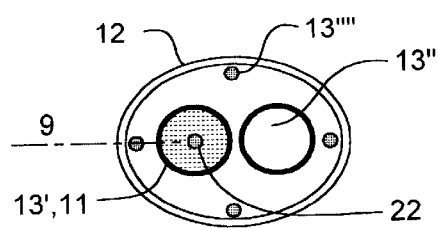
FIG. 7B
FIG. 7C
FIG. 7A

STOMACH TREATMENT APPARATUS AND METHOD

Cross-Reference to Related Application

This application claims priority to Application No. 60/120,781, entitled STOMACH TREATMENT APPARATUS AND METHOD, filed Feb. 19, 1999.

BACKGROUND OF THE INVENTION

1. Field of the Invention

This invention relates generally to an apparatus and method for the treatment of the stomach. More specifically, the invention relates to an apparatus and method to reduce the distensibility and/or volume of the stomach to treat obesity and other eating disorder related conditions.

2. Description of Related Art

Currently, a large segment of the American population suffers from eating disorders which can cause obesity, bulimia and anorexia leading to a number of disease states both physical and psychological. Since the advent of processed foods with designer taste addition, obesity has become prevalent in every geographic area of the United States. The snack food slogan, "you cannot eat just one" has become a reality. Modification of excessive dietary intake is a multibillion-dollar industry.

There are many severe health consequences of obesity including heart disease, stroke and diabetes all of which can result in death, morbidity and/or significant quality of life issues. Related health conditions include gastroesophageal reflux (GERD) which is caused from regurgitation of gastric contents into the esophagus is aggravated by excessive food intake typical of compulsive eating and other eating disorders associated with the obese patient. These contents are highly acidic and potentially injurious to the esophagus resulting in a number of possible complications of varying medical severity. The reported incidence of GERD in the U.S. is as high as 10% of the population. Acute symptoms of GERD include heartburn, pulmonary disorders and chest pain. On a chronic basis, GERD subjects the esophagus to ulcer formation, or esophagitis and may result in more severe complications including esophageal obstruction, significant blood loss and perforation of the esophagus. Severe esophageal ulcerations occur in 20–30% of patients over age 65.

Current medical management has not been able to successfully intervene to significantly reduce the incidence of obesity within the U.S. For example, pharmacological modification with diet suppressants has been associated with significant metabolic side effects. Various attempts to reduce the volume of the stomach through surgical intervention or indwelling devices have had limited effectiveness with significant drawbacks. For example, in the morbidly obese, surgical intervention with gastric stapling, gastric banding and ileo-jejunal bypass has been abandoned because of the severe short-term surgical complications and the long-term side effects of surgically induced malabsorption and/or the potential for gastric obstruction. Other attempts to reduce the volume of the stomach through the use of indwelling gastric balloons have had only limited effectiveness in combatting the dietary rages of these patients. Such devices are prone to failure due to the extremely corrosive/acidic environment of the stomach. Once placed, they can not be readily modified or adjusted to meet the changing eating patterns and dietary needs of the patient. Also, they fail to address the significant problem of injurious contact with the gastric mucosa that can result from leaving an inflated bag in the stomach for an extended period of time. Moreover, these devices and approaches present the potentially fatal risks of gastric obstruction and infection from the indwelling device. Finally, due to combination of one or more of gastric wall contact, gastric obstruction and bacterial infection, such devices present a significant risk of causing gastric ulcers.

The present therapies for GERD include pharmacological, surgical and minimally invasive treatment. Despite marginal success, all have clinical limitations and none adequately treat the disease or address the patient's need to reduce ingested food. Current drug therapy for GERD includes histamine receptor blockers which reduce stomach acid secretion and other drugs which may completely block stomach acid. However, while drugs may provide short-term relief, they do not address the underlying cause of LES dysfunction. They also present the disadvantage of adverse side affects as well as requiring the patient to remain on long term drug therapy which is often cost prohibitive. Surgically invasive procedures requiring percutaneous introduction of instrumentation into the abdomen exist for the surgical correction of GERD. One such procedure, Nissen fundoplication, involves constructing a new "valve" to support the LES by wrapping the gastric fundus around the lower esophagus. Although the operation has a high rate of success, it is an open abdominal procedure with the usual risks of abdominal surgery including: postoperative infection, herniation at the operative site, internal hemorrhage and perforation of the esophagus or of the cardia. A 10-year study reported the morbidity rate for this procedure to be 17% and mortality 1%. This rate of complication drives up both the medical cost and convalescence period for the procedure and excludes significant portions of certain patient populations (e.g., the elderly and immuno-compromised).

Efforts to perform Nissen fundoplication and related sphincteroplasty procedures by less invasive techniques have resulted in the development of laparoscopic Nissen fundoplication and related laparoscopic procedures. Other attempts to perform fundoplication involve fastening of the invaginated gastroesophageal junction to the fundus of the stomach via a transoral approach using a remotely operated fastening device, eliminating the need for an abdominal incision. However, this procedure is still traumatic to the LES and presents the postoperative risks of gastroesophageal leaks, infection and foreign body reaction, the latter two sequela resulting when foreign materials such as surgical staples are implanted in the body.

While the methods reported above are less invasive than an open Nissen fundoplication, some still involve making an incision into the abdomen and hence the increased morbidity and mortality risks and convalescence period associated with abdominal surgery. Others incur the increased risk of infection associated with placing foreign materials into the body. All involve trauma to the LES and the risk of leaks developing at the newly created gastroesophageal junction. Other noninvasive procedures for tightening the LES still do not solve the fundamental problem of reducing the patient's ability to overeat and cause an overproduction of stomach acid which results in acid reflux. It is predicted that such a reduction can ameliorate gastroesophageal reflux without direct modification of the sphincter and the resulting complications.

In order to more fully appreciate the issue involved in the treatment of obesity and the diagnosis and treatment of obesity-related conditions a description of the anatomy of the stomach and adjoining structures will now be presented.

Referring to FIGS. 1A and 1B, the anatomy of the stomach can be divided into different segments on the basis of the mucosal cell types in relation to external anatomical boundaries. The cardiac segment is immediately subjacent to the gastroesophageal junction and is a transition zone of the esophageal squamous epithelium into the gastric mucosa. The fundus is the portion of the stomach that extends above the gastroesophageal junction. The body or corpus of the stomach extends from the fundus to the incisura angularis on the lesser curvature of the stomach. The majority of parietal acid forming cells are present in this segment. The fundus and the corpus function as the main reservoir of ingested food. The antrum extends from the lower border of the corpus to the pyloric sphincter. The majority of gastrin producing or G-cells are present in the antral mucosa. The main blood supply is variable but typically courses from the celiac axis into the gastric and gastroepiploic arcades. Nutrient vessels to the stomach coarse from the vascular arcades of the greater and lesser curvatures. These vessels penetrate the gastric wall in a perpendicular fashion and arborize horizontally in a dense vascular plexus throughout the wall of the stomach. For the most part, gastric innervation is provided by the vagus nerves which form a plexus around the esophagus and then reform into vagal trunks above the esophageal haitus. An extensive myenteric plexus is formed within the muscular wall of the stomach. Impulses from stretch or tension receptors within the gastric wall are transmitted to the nucleus tractus solitaris of the brain stem by afferent vagal fibers. These stretch/tension receptors within the fundus and corpus detect gastric distension or gastric pressure from ingested food. Recent studies appear to favor the role of gastric tension instead of gastric distension as the main elicitor of satiety. A smaller and less defined contribution is provided by sympathetic fibers from the celiac plexus. Within the submucosal layer, these fibers form Meissner's plexus may regulate mucosal secretion and absorption.

The four basic components of the gastric wall are the mucosa, submucosa, muscularis and the serosa. These four components are found throughout the entire gastrointestinal tract. The mucosa consists of mucus secreting columnar epithelium that invaginates into glands. The cellular components of the glands vary within each segment of the stomach. The parietal or acid producing cells are mainly located within the gastric glands of the fundus and corpus. These exocrine cells also produce intrinsic factor that binds with vitamin B12 to facilitate absorption in the small intestine. Failure by the parietal cells to produce intrinsic factor leads to pernicious anemia, a condition commonly seen with atrophy of the gastric mucosa. The subjacent layer is frequently subdivided into the lamina propria, the muscularis mucosa and the submucosa. With the exception of the thin muscularis mucosa, this subjacent layer consists of collagen containing connective tissue. The next layer, the muscularis externa, consists of smooth muscle which propels food forward in the digestive tract. The muscularis is typically subdivided into two layers of circular and longitudinal fibers. An oblique layer of muscle fibers between the circular and longitudinal layers is typically present in the stomach. Auerbach's myenteric plexus of parasympathetic fibers is contained within the muscularis externa. The fourth layer serosa is a dense outer covering of connective tissue that merges into the peritoneum.

Although subdivided into five anatomical segments, the physiological function of the stomach is described in two main components. The proximal third is termed the fundus which includes the corpus and fundus as a single functioning reservoir of ingested food. Smooth muscle cells of the physiological fundus have a lower resting potential that inhibits rapid depolarization and contraction. Instead, fundic muscle exhibits an active tone at rest that pushes ingested food into the antrum. The fundus also exhibits the phenomenon of receptive relaxation in which resting tone is decreased to accommodate the recently ingested bolus. The distal two-thirds of the stomach is termed the antrum which propels the partially digested food into the duodenum. Antral smooth muscle cells possess a higher resting potential that leads to rapid depolarization. Pacesetter potentials are initiated from the interstitial cells of Cajal that are located along the proximal aspect of the greater curvature. A wave of rapid depolarization is created within the antral smooth muscle that results in a type 2 peristaltic contraction. In contradistinction to the fundus, a resting tone is not exhibited in the antrum. The initiation of a fed pattern of gastric motility involves a complex interaction of locally released hormones with intrinsic and extrinsic neural pathways that are mediated through the vagus nerves.

A variety of non-invasive methods to study gastric motility evaluation are available although they include technical drawbacks and limitations. Contrast cinefluoroscopy with a barium meal has been used extensively for animal research but has limited application in humans due to exposure from ionizing radiation. Gastric intubation techniques can provide objective data on distensibility and motility with manometric/strain gauge transducers. Impedance epigastrography measures electrical patterns of gastric emptying. More recently, high resolution/real time ultrasonic imaging has provided a convenient non-invasive methodology to view gastric motility.

Currently a need exists for an efficacious minimally or non-invasive apparatus that is able to treat eating disorder related obesity. A further need exists for a non-invasive device that is able to reduce the distensibility and/or volume of the stomach. Still a further need exists for a non-invasive apparatus that is able to produce appetite suppression.

SUMMARY OF THE INVENTION

Accordingly, in view of the above presentation it is an immediate object of this invention to provide an apparatus and method for treating eating-disorder obesity that overcomes the deficiencies and omissions associated with the prior art.

Another object of the present invention is to provide an apparatus to treat the stomach and reduce the distensibility of the stomach.

Still another object of the invention is to provide an apparatus to treat the stomach and reduce the volume of the stomach.

Yet another object of the invention is to provide an apparatus to treat the stomach and produce appetite suppression.

Still yet another object of the invention is to treat the stomach without damaging a mucosal lining of the stomach.

Yet another object of the invention is to treat the stomach and produce a perception of stomach fullness with a reduced volume of food in the stomach.

These and other objects of the invention are achieved in an apparatus to modify a stomach wall comprises an elongated member including at least one lumen. A deployable member is coupled to the elongated member. The deployable member is configured to be advanceable and removable from the stomach in a non-deployed state and sized to be positioned in the stomach in a deployed state to engage at least portions of the stomach wall. The deployable member is further configured to house a fluidic media and at least portions of the deployable member wall is configured to be cooled by the fluidic media. The deployable member has a contour in the deployed state approximating at least a portion of a stomach. A microwave antenna is movably positioned in the deployable member so as to control a microwave field strength vector in relation to the antenna. The microwave antenna is configured to be coupled to a microwave energy source and deliver microwave energy to a selectable tissue site in the stomach wall while minimizing thermal injury to one of a mucosal or a submucosal layer. A cable member is coupled to the microwave antenna and is configured to be advancecable within the elongated member.

In another embodiment, the wound healing response is a circumferential wound healing response and includes deposition of scar collagen within the gastric wall.

In yet another embodiment, the energy delivery device is coupled to a cooling media. The cooling media cools a selected tissue site within the stomach wall to preserve the mucosal layers of the stomach during the delivery of energy from the energy delivery device.

BRIEF DESCRIPTION OF THE DRAWINGS

FIG. 2A depicts a lateral view of an embodiment of the stomach treatment apparatus illustrating components of the apparatus and its placement and use in treating the stomach and stomach wall.

FIG. 2B is a lateral view illustrating a shaped expansion member including a first and second radius of curvature.

FIG. 4A is a lateral view of an embodiment of a linear coaxial microwave antenna.

FIG. 4B is a lateral view of a microwave antenna illustrating various parameters and attributes of the microwave beam.

FIG. 7A is a lateral view of an embodiment of the apparatus having a double jointed or articulated shaft.

FIGS. 7B and 7C are cross-sectional views of the elongated shaft of embodiments from FIG. 7A illustrating coaxial and eccentric placement of the antenna cabling and cooling channels.

DETAILED DESCRIPTION

Figure 1A:
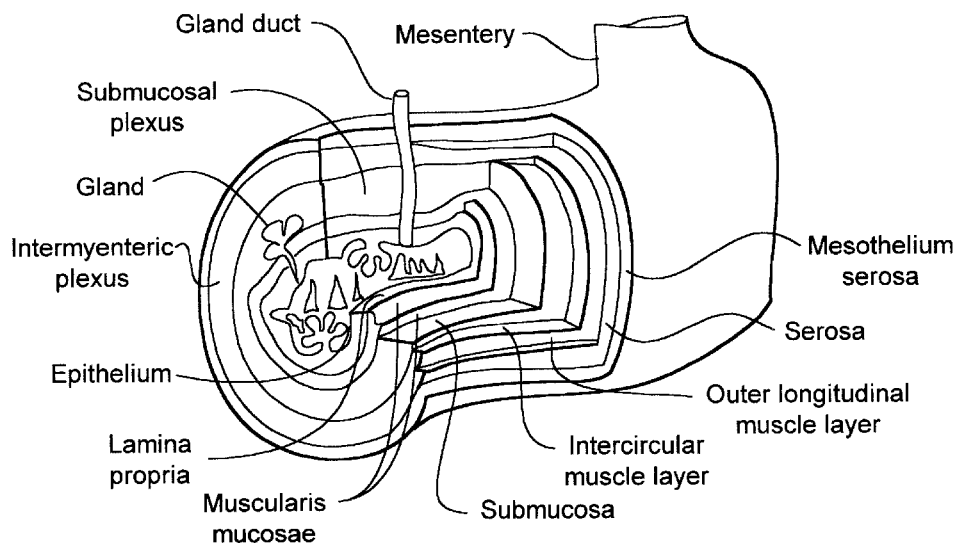
FIG. 1A is a cross-sectional view of the stomach wall illustrating the anatomy of the stomach wall.
Figure 1B:
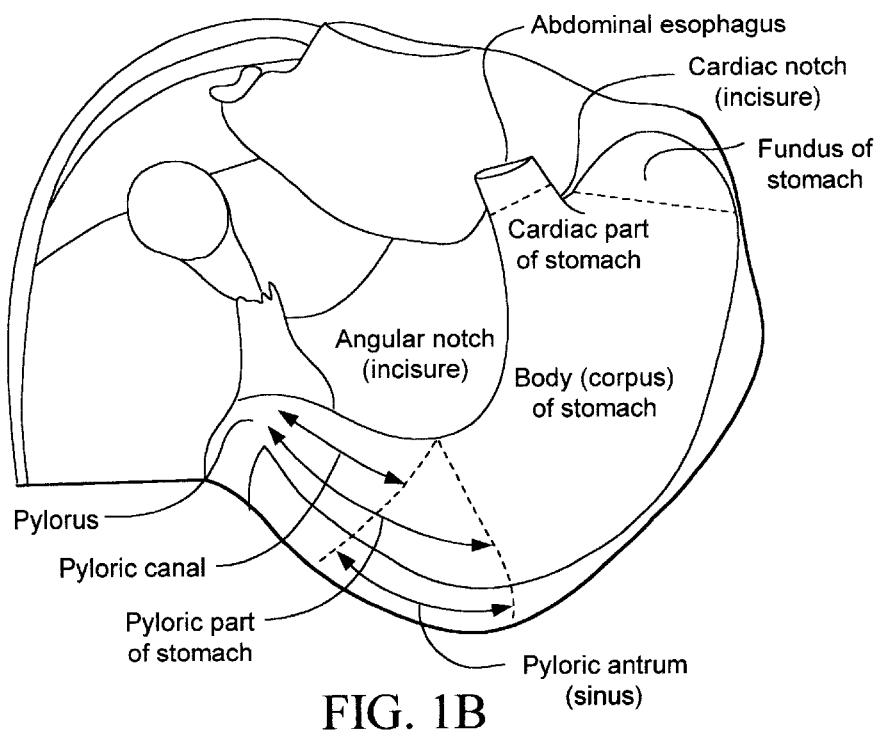
FIG. 1B is a perspective view of the stomach illustrating the anatomical regions of the stomach.

The present invention provides an apparatus and method to treat the stomach and other organs and tissue within the gastro-intenstinal tract through the delivery of thermal energy to the stomach wall to cause a contraction or reduction in volume of the stomach or other selected tissue. In various embodiments, the present invention can be configured to heat a broad submucosal layer of tissue within the stomach wall without thermal damage (e.g. burning, protein denaturization, etc.) of the mucosa of the stomach or other selected organ. A thermal lesion is created within the wall of the stomach without mucosal burning. The delivery of energy can be configured to result in an immediate contraction of the preexisting collagen matrix of the stomach wall or it may result in a delayed initiation of a wound healing sequence. One or both of these effects can serve to reduce both distensibility and volume of the stomach.

With a wound healing sequence, soft tissue contraction is achieved via myofibroblastic contraction that is secured with subsequent deposition of a static-supporting matrix of scar collagen. The key functional effects of the wound healing response are either i) to reduce gastric distensibility with the deposition of a static supporting matrix of collagen, or ii) to reduce overall gastric volume by contracting the subserosal layers of the stomach. Resistance to stomach distension from either effect will be neurologically interpreted as a full stomach. For many patients, a reduction in stomach distensibility without reduction in overall gastric volume will be sufficient to produce a full stomach sensation due to a centrally mediated neurological response of the vagus nerve. The ability to sequentially titrate the perception of stomach distention will be an important factor when accounting for personal variations in appetite from one patient to the next. The invention can also be used to restrict or otherwise control the outflow of contents from the pylorsus. Moderate restriction to outflow at the pylorus may also enhance feedback sensation of a "full stomach". The perception of distention with smaller caloric loads is the key therapeutic effect for weight reduction and subsequent weight control.

Referring now to FIG. 2A, in an embodiment of the present invention, a stomach treatment apparatus 10 includes an elongated member or shaft 12 coupled to an expansion device 14, in turn coupled to an energy delivery device 16 configured to deliver energy to a selected tissue site 18 in a hollow structure of the body including the stomach 20 and produce lesions and/or tissue contraction sites 21 within stomach wall 20' while preserving mucosal layer 20". In various embodiments, energy delivery device 16 can be coupled to an energy source 17.

At least portions of apparatus 10 may be sufficiently radiopaque in order to be visible under fluoroscopy and/or sufficiently echogenic to be visible under ultrasonography and the like. Also as will be discussed herein, apparatus 10 can include visualization capability including, but not limited to, a viewing scope, an expanded eyepiece, fiber optics, video imaging and the like. Such viewing means may be delivered through a central lumen 13 within elongated shaft 12.

Shaft 12 (also called catheter 12) has a proximal and distal end 12' and 12" and has sufficient length to position expansion device 14 in the stomach using a transoral approach. Typical lengths for shaft 12 include, but are not limited to, a range of 40–220 cms. Shaft 12 can also be coupled at its proximal end to a handpiece 15, which in various embodiments can include various ports for the delivery of gases, liquids and other media. In various embodiments, shaft 12 is flexible, articulated and steerable and can contain fiber optics (including illumination and imaging fibers), fluid and gas paths, and sensor and electronic cabling. In one embodiment, shaft 12 can be a multi-lumen catheter, as is well known to those skilled in the art. In various embodiments shaft 12 can be fabricated from a variety of medical grade resilient polymers including polyethylene (including HIPDP, LDPE, HDPE/LDPE blends and irradiated HDPE), polyurethane, Pebax®, silicone, polyimide and other thermoplastics and elastomers known in the art. Shaft 12 can also include a reinforcing braid or spiral which serves to increase longitudinal, torsional (e.g. pushability and torqueability), and hoop stiffness which reduces kinking and preserves the patency of lumens 13. Braiding involves reinforcing the shaft 12 with a reinforced wire mesh that is typically composed of 8 or 16 individual wire elements. Common flat wire braid sizes can include: 0.0005"×0.003", 0.0007"×0.003", 0.0007"×0.0005", 0.001"×0.003", 0.001"×0.005", and larger. Round wire braid sizes can include: 0.001", 0.0015", 0.002", and larger. Spiral reinforcement involves radially winding one or more flat or round wire elements within or on the surface of the shaft wall. Typical braid/spiral wire materials can include stainless steel, copper, and other ferrous and nonferrous materials. Spiral reinforcement may be selected for applications requiring increased kink resistance and lumen patency versus but not as much as longitudinal or torsional stiffness as braided application.

In various embodiments, elongated shaft 12 may have one or more lumens 13 which can be configured for the advancement of medical imaging/visualization devices such as fiber optic view scopes and the like. Lumens 13 can also be configured for the delivery of liquids (including cooling liquids), gases and medicaments. In one embodiment lumen 13 can be configured as an inflation lumen to inflate expansion device 14 using a liquid or gaseous inflation media.

Expansion device 14 has an expanded and non-expanded state and is configured to be positionable within the stomach. More specifically, expansion device 14 is configured in its expanded state to contact all or a portion of an interior surface or gastric mucosa 20" of stomach wall 20'. This can be facilitated by expansion device 14 having an inflated diameter sufficient to expand the stomach to an amount sufficient to at least partially efface and/or straighten the folds of the internal surface 20" of the stomach.

In various embodiments, expansion device 14 can be an inflatable balloon as is well known in the medical device art. Balloon 14 has an external surface 14', an internal surface 14", a proximal end 14'" and a distal end 14"". Balloon 14 is inflated using gas or liquid inflation media delivered via means of an inflation lumen 13 disposed within elongated member 12 fluidically coupled to balloon 14, preferably at or near proximal end 14'". In various embodiments, balloon 14 can be formed/blown at the distal end 12" of catheter 12 or can be attached using heat sealing or other balloon attachment method well known in the art.

In various embodiments, balloon 14 can have a variety of shapes including spherical, crescent, or oval. Referring now to FIG. 2B, balloon 14 can also have a shape/contour 33 approximately that of the oblong internal contour of the human stomach or other portion thereof including but not limited to, the antrum, corpus, fundus, cardia, pylorus, or the pyloric region. In a specific embodiment, balloon 14 can have a first and a second radius of curvature 35, 37 that are substantially parallel over least a portion of their respective lengths and can approximate the lesser and a greater curvatures of the stomach. Balloon 14 can also be configured to be translucent to microwaves or otherwise non-absorbing and non-reflecting to microwave radiation. In various embodiments, this can be achieved through the selection of balloon materials and dimensions (e.g. diameter, wall thickness, etc). Also, various thermoplastics or elastomers known in the art to have low microwave absorption characteristics may be selected.

The compliance of balloon 14 can be selected (through choice of balloon materials, balloon wall thickness, balloon shape, etc) such that balloon 14 expands and conforms to fill all or a portion of stomach 20 making uniform contact with gastric mucosa 20" including crevices and folds 20'". This can be achieved by the use of compliant balloon materials described herein. In one embodiment the compliance of balloon 14 is selected to be less than that of the stomach wall 20'. Alternatively, the compliance of balloon 14 can be selected such that when balloon 14 is expanded it expands the internal volume of the stomach and/or stretches the stomach wall 20'. This can be achieved by setting the compliance of balloon 14 to be equal to or greater than the compliance of the stomach wall 20' through the use of non-compliant materials described herein.

All or a portion of balloon 14 can be made of a non-compliant material (as is known in the art) in order to achieve a predictable fixed balloon diameter. In various embodiments, such non-compliant materials can include PET, irradiated polyethylene, polyurethane and others known in the art. In alternative embodiments, balloon 14 can be configured to have an adjustable diameter (e.g. pressure compliant) by constructing all or a portion of balloon 14 from compliant materials. Such compliant materials include latex, silicone, and other thermoplastics and elastomers known in the art.

Turning now to a discussion of energy delivery, suitable energy sources 17 and energy delivery devices 16 that can be employed in one or more embodiments of the invention include: (i) a radio-frequency (RF) source coupled to an RF electrode, (ii) a coherent source of light coupled to an optical fiber, (iii) an incoherent light source coupled to an optical fiber, (iv) a heated fluid coupled to a catheter with a closed channel configured to receive the heated fluid, (v) a heated fluid coupled to a catheter with an open channel configured to receive the heated fluid, (vi) a cooled fluid coupled to a catheter with a closed channel configured to receive the cooled fluid, (vii) a cooled fluid coupled to a catheter with an open channel configured to receive the cooled fluid, (viii) a cryogenic fluid, (ix) a resistive heating source coupled to a heating element positioned on or within the balloon 14, (x) a microwave source led to an ultrasound emitter, wherein the ultrasound power source produces energy in the range of 300 KHz to 3 GHz.

For ease of discussion for the remainder of this application, the energy source 17 utilized is a microwave energy source, and energy delivery device 16 is a microwave antenna 16. The use of microwave energy is well suited to the stomach because it produces a more uniform field over a larger area than other forms of energy. When antenna 16 is energized by microwave generating source 17, antenna 16 emits electromagnetic energy which causes heating of tissue within stomach wall 20' at target location 18.

In various embodiments, microwave energy source 17, emits energy in a frequency range that includes, but is not limited to, 915 MHz to 2.45 GHz. In a preferred embodiment microwave power source 17 emits microwave energy at a preferred frequency of 1300 MHz+−50 MHz, and at power levels adjustable up to 50 or 100 watts. Accordingly, the microwave energy source 17 is capable of generating microwaves at a frequency of 1,300 MHz+−50 MHz and can be set at a precise frequency value within this range.

Figure 3:
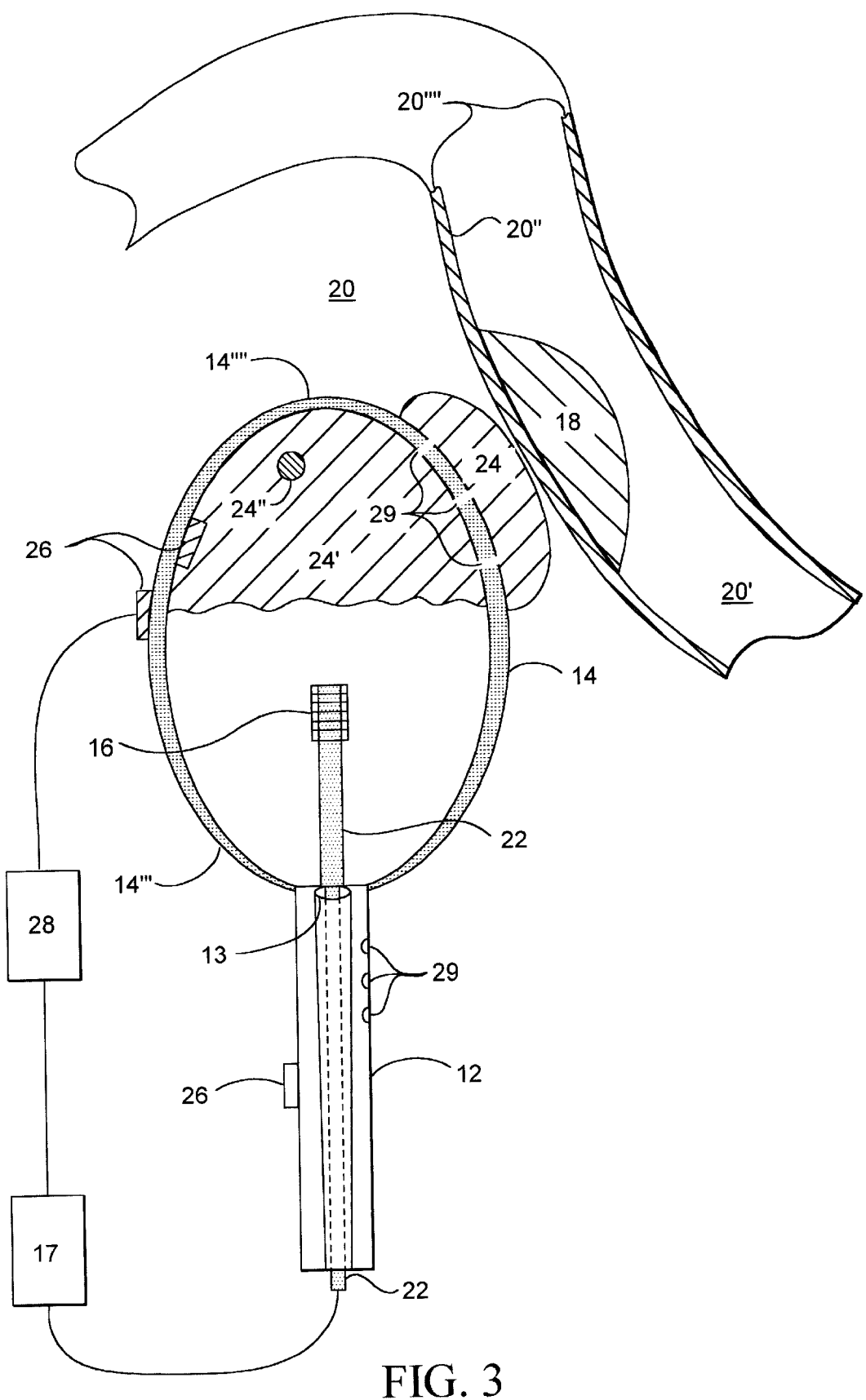
FIG. 3 is a lateral view of an embodiment of the stomach treatment apparatus illustrating the use of a dipole microwave antenna, cooling solution and cooling apertures.

Referring now to FIGS. 3, 4A and 4B, in various embodiments microwave antenna 16 can be a linear coaxial microwave antenna with a choke or a standard single junction dipole microwave antenna. The dipole microwave antenna 16 can be constructed from a flexible coaxial cable 22 having an inner conductor 22' covered by an inner insulation layer 22", an outer conductor 22''' and an outer insulating jacket 22"". Coaxial cable 22 from which the antenna 16 is formed extends from the proximal end of elongated member 12 and terminates in a slotted radiating portion 19 of antenna 16. In various embodiments antenna 16 and coaxial cable section 22 within balloon 14 may have a double joint articulation. The operation of the dipole microwave antenna 16 as is utilized in one embodiment of the apparatus of the present invention is described more fully in U.S. Pat. No. 4,825,880 to Stauffer et. al. for an Implantable Helical Coil Microwave Antenna, which is incorporated herein by reference.

Coaxial cable 22 can be disposed within elongated member 12 (via a lumen 13) and extend from proximal end 12' distally into balloon 14 including proximal or distal portions 14''' and 14"" or a section there between. Coaxial cable 22 can be coupled to microwave energy source 17 via an electronic connector (such as a lemo connector or other connector known in the art) in the proximal portion 12' of member 12 including handpiece 15. In one embodiment antenna 16 is tethered or otherwise fixed to the distal end 14"" of balloon 14 to assure centralization of the device within the stomach. In alternative embodiments, microwave antenna 16 is movable within balloon 14 by advancement of coaxial cable 22. In this embodiment the length of antenna 16 can be increased or decreased in length by a sliding a sheath 11 of microwave absorbable material/insulation (which can be an inner member discussed herein) over antenna 16. This configuration provides means for controlling the emitted power levels, the direction and strength (e.g. field strength vector) of the microwave beam/field.

In various embodiments, antenna 16 can be configured to produce one or more of the following types of antenna/microwave beams 31: omnidirectional, pencil-beam, flat-top flared beam and the asymmetrically flared beam. In a preferred embodiment, antenna 16 is configured to produce an omnidirectional beam. In related embodiments, antenna 16 can be configured to produce a beam 31 with a selectable beam arc 31' and selectable microwave field strength beam vector 31". Beam arc 31' can be selected from 1 to 360°.

The arc 31' and direction of beam 31 can be controlled or modified using one or more approaches. In an embodiment the directivity and field vector 31" of antenna 16 can be controlled by varying the length of antenna 16 through the use of sliding sheath 11. In another embodiment, the directivity of beam 31 including an omnidirectional beam can be increased through the use of an array 16' of radiating elements 16" built up along the symmetry axis 31''' of beam 31. In various embodiments these or other approaches can be used to select beam arc 31' from 1 to 360°, with specific embodiments of 30, 45 60, 90, 120, 180 and 270°.

Antenna 16 is configured to minimize impedance mismatches as measured by VSWR (voltage standing wave ratio) of cable 22 and/or antenna 16. This can be accomplished by controlling the length of the dipole elements to a fraction (e.g. ¼ or ½) of the microwave wavelength used or through the use of a slow wave structure antenna described herein. In various embodiments, a cooling media 24 can partially or completely fill balloon 14 (via lumen 13") and/or all or a portion of lumens 13. Cooling media 24 can serve to cool antenna 16, cable 22 and tissue site 18. In one embodiment, cooling media 24 can be chilled water 24 which can be chilled to temperatures approaching 32° F. using a refrigeration device or a recirculating water chilling device, (not shown) well known in the art.

In an alternative embodiment, antenna 16 can have a "slow wave structure" and the length of two dipole elements can be shorter or longer than ¼ of the wavelength of the microwave frequency used. One such slow wave structure is described in U.S. Pat. No. 4,495,503 to Morman which is incorporated by reference herein.

Figure 5A:
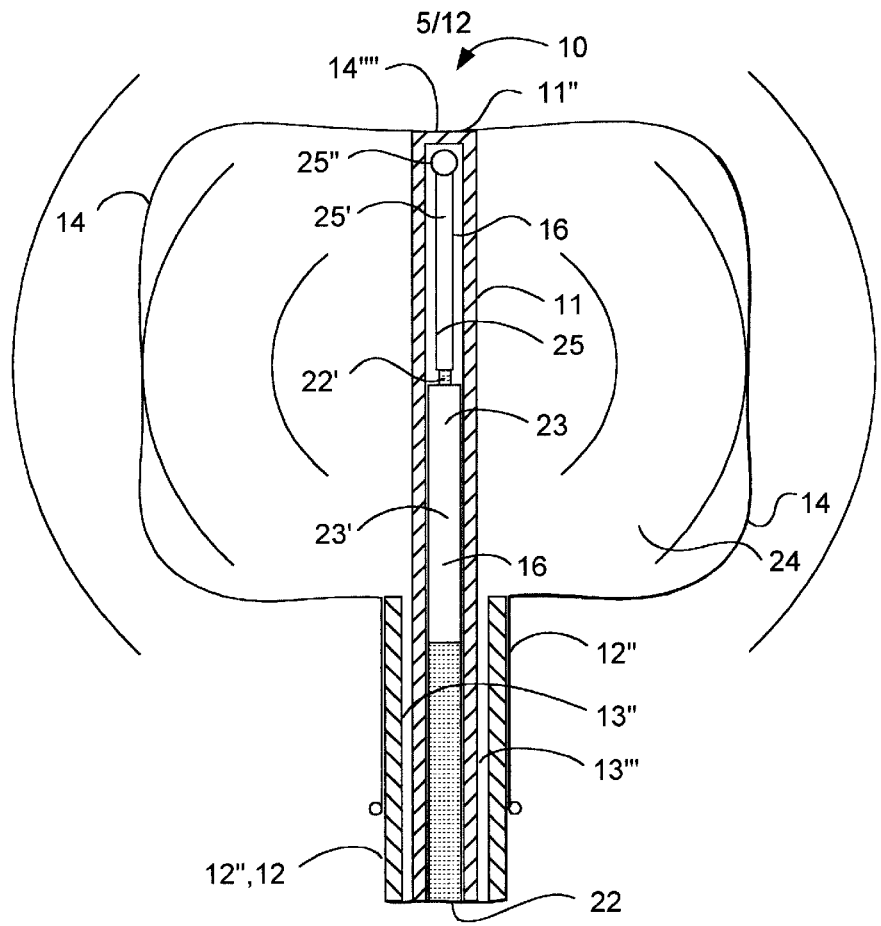
FIG. 5A is a lateral view of the distal portion of the apparatus illustrating the juncture between the inner member and balloon, a dipole microwave and cooling channels.
Figures 5B, 5C:
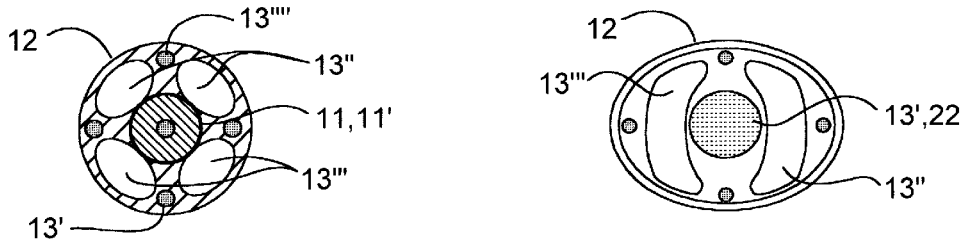
FIG. 5B is a cross-sectional view of the elongated shaft illustrating lumens for cooling, steering wires, antenna cabling and fiber optics.
FIG. 5C is a cross-sectional view of an oval elongated shaft illustrating placement of cooling lumens in a surrounding relation to the antenna cabling.
Figure 5D:
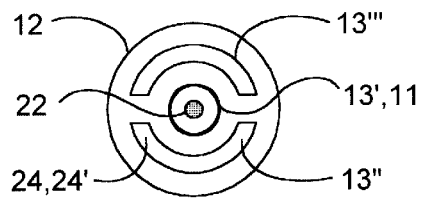
FIG. 5D is a cross-sectional view of the elongated shaft illustrating semicircular cooling lumens.

An alternative embodiment of balloon 14 and antenna 16 is shown in FIGS. 5a and 5b. In this embodiment, balloon 14 can be made out of a latex material or other elastomer and is attached (by adhesive bonding, heat sealing other plastic bonding method known in the art) to the distal end 12" of elongated shaft 12. This embodiment also includes an inner member 11 that is positioned within a lumen 13' of shaft 12. Inner member 11 includes a lumen 11' that is configured (e.g. of sufficient inner diameter, etc.) to receive and allow the axial advancement of coaxial cable 22, including antenna 16. Inner member 11 may also be configured to receive and allow the advancement of a fiber optic viewing device as well. In a preferred embodiment, lumen 13' is concentric with respect to the circumference of elongated shaft 12; and inner member lumen 11' is concentric with respect to the circumference of inner member 11 and/or elongated shaft 12. All or a portion of the length of shaft 12 (including the wall of lumens 13' and/or 11') can include microwave absorbable materials known in the art to reduce/prevent microwave emissions from sections of cable 22 other than antenna 16.

In various embodiments, inner member 11 can be fixed or configured to be advanceable within shaft 12. In one embodiment, shown in FIG. 5A, the distal end 11" of the inner member is attached (using a medical grade adhesive or other bonding method known in the art) to the distal end 14"" of balloon 14. Inner member 11 can be made of a variety of resilient medical polymers known in the art including polyimide, irradiated polyethylene, polyurethane, or Pebax® and other thermoplastics. Inner member 11 can also be reinforced with a wire braid or coil (discussed herein) that may be embedded or on the surface of member 11. The coil or braid serves to strengthen longitudinal and torsional stiffness (e.g. pushability and torqueability) of inner member 11 and preserve lumen integrity/patency.

For the embodiments shown in FIGS. 5–8, antenna 16 is comprised of two dipole elements. The first dipole element 23, consists of a conductive cylinder 23' positioned over a distal section of coaxial cable 22 that has its outer jacket 22"" removed. More specifically, cylinder 23' is fixedly positioned over outer conductor 22'" of coaxial cable 22 using soldering, brazing, crimping or a metal joining method known in the art. The second dipole element 25 consists of a metal cylinder 25' with a metal ball 25" attached (via soldering or brazing) at its distal end. Metal cylinder 25' is fixedly positioned over the distal most section of inner conductor 22' which extends distally from the distal end of the first dipole element 23. Metal cylinder 25' is attached to inner conductor 22' using soldering, brazing, crimping or metal joining method known in the art. In a preferred embodiment, both first and second dipole elements 23 and 25 have axial lengths one quarter of the wavelength of the microwave frequency transmitted to antenna 16. In preferred embodiments, this frequency is 915 MHz or 2.45 GHz. Cylinders 23' and 25' and ball 25" can be fabricated from a variety of conducting metals including, but not limited to, aluminum, stainless steel, gold, platinum, copper and combinations thereof. Ball 25" serves to disperse/reduce current density at the tip of cylinder 25' and to reduce and/or prevent excessive heating and/or arcing from dipole element 25.

Referring now to FIG. 5b which shows a cross section of elongated shaft 12, shaft 12 can include separate lumens 13 for the inflow and the outflow of cooling media 24 and for the advancement of coaxial cable 22, steering wires, the inner member, and a fiber optic view assembly. All or a portion of lumens 13 can be concentric or nonconcentric with respect to the circumference of shaft 12. In this and related embodiments, shaft 12 includes lumens 13' for the advancement of coaxial cable 22 and/or inner member 11; lumens 13" and 13'" for the inflow and return of cooling media 24 to cool antenna 16, balloon 14 and cable 22; and lumens 13"" for steering and pull wires and the like. In the embodiment shown in FIGS. 5a–b, lumen 13' is concentrically positioned with respect to shaft 12 and other lumens 13", 13'" and 13"" are radially distributed around the center of lumen 13'. Lumen 13' preferably has a substantially circular cross section and has sufficient diameter to allow the passage of inner member 11 or coaxial cable 22 and a fiber optic viewing device. Lumens 13", 13'" and 13"" can have a substantially oval, circular or crescent cross section. For multilumen embodiments of catheter 12, the integrity/patency of lumens 13 can be maintained with the use a reinforcing braid or coil (discussed herein) embedded or on the surface of shaft 12. In various embodiments, the inner diameter of lumens 13 can range from 1–40 mm with specific embodiments of 3, 5 and 20 mm. In various embodiments, shaft 12 can have an outside diameter in the range 3–50 mm, with specific embodiments of 11 and 12, 15 and 20 mm.

Referring now to FIG. 5c (a cross-sectional view of shaft 12), in one embodiment, cooling lumens 13" and 13'" can be configured to surround a substantial portion (about 75%) of the circumference of inner member lumen 13' or inner member 11 or coaxial cable 22. In this embodiment, when cooling lumens 13" and 13'" are filled with a liquid cooling media 24, cooling lumens 13" and 13'" absorb any unwanted microwaves radiating out of coaxial cable 22 or antenna 16. To facilitate surrounding of the circumference of lumen 13', lumens 13" and 13'" can have a partial kidney or oval shape. In a specific embodiment shown in FIG. 5d, lumens 13" and 13'" can be at least partially semicircular and can share the same locus as lumen 13'. The use of liquid filled cooling lumens for the absorption of microwave radiation is described more fully in U.S. Pat. No. 5,776,176 to Rudie, which is incorporated by reference herein. The present invention provides the improvement of using enhanced microwave absorbable liquids, compounds, particles, etc. (described herein) in order to be able titrate/control the amount of microwave absorption. The present invention also provides the improvement of the use of microwave absorbable compounds (described herein) which increase their microwave absorbing qualities with an increase in temperature or microwave power.

Figure 6A:
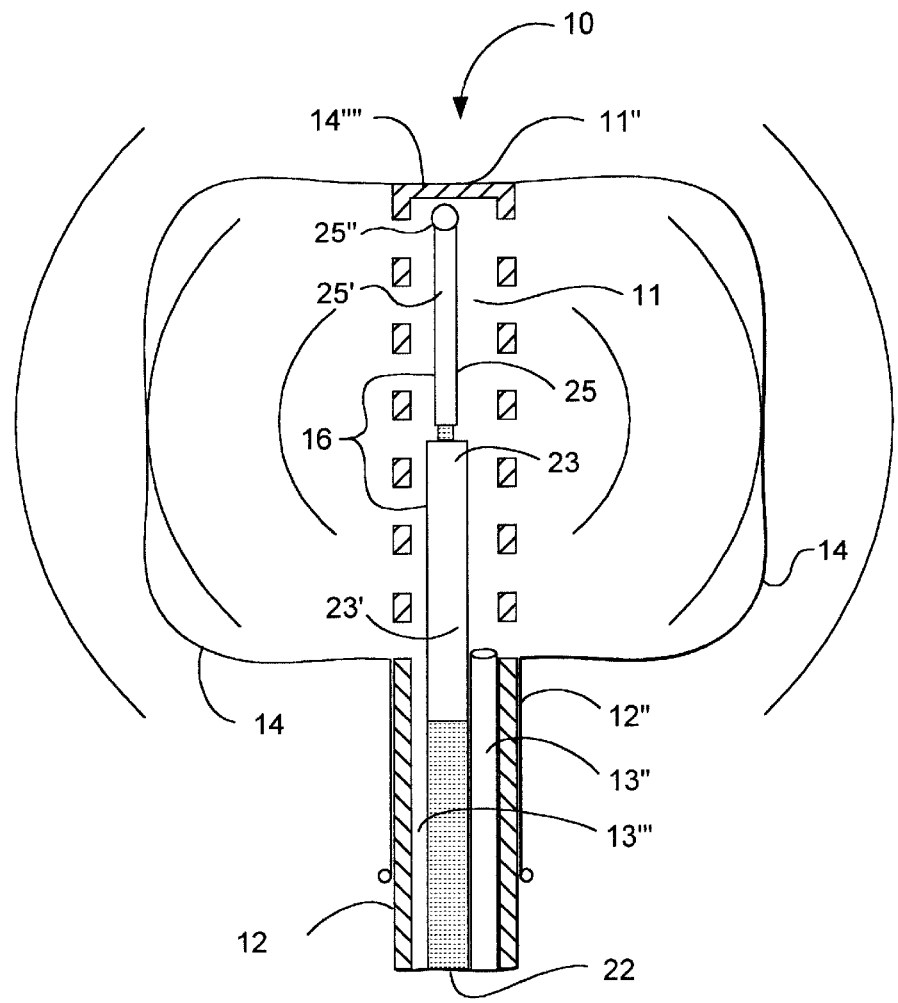
FIG. 6A is a lateral view of the distal portion of an embodiment of the apparatus having a non-coaxial/eccentric placement of the inner member and cooling channels.
Figure 6B:
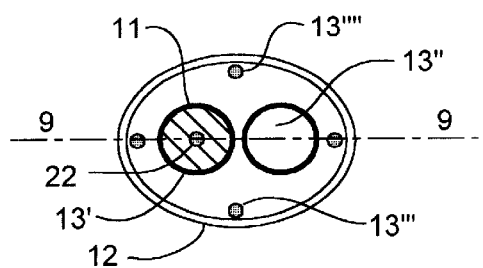
FIG. 6B is a cross-sectional view of the elongated shaft of the embodiment from FIG. 6A.
Figures 8A, 8B:
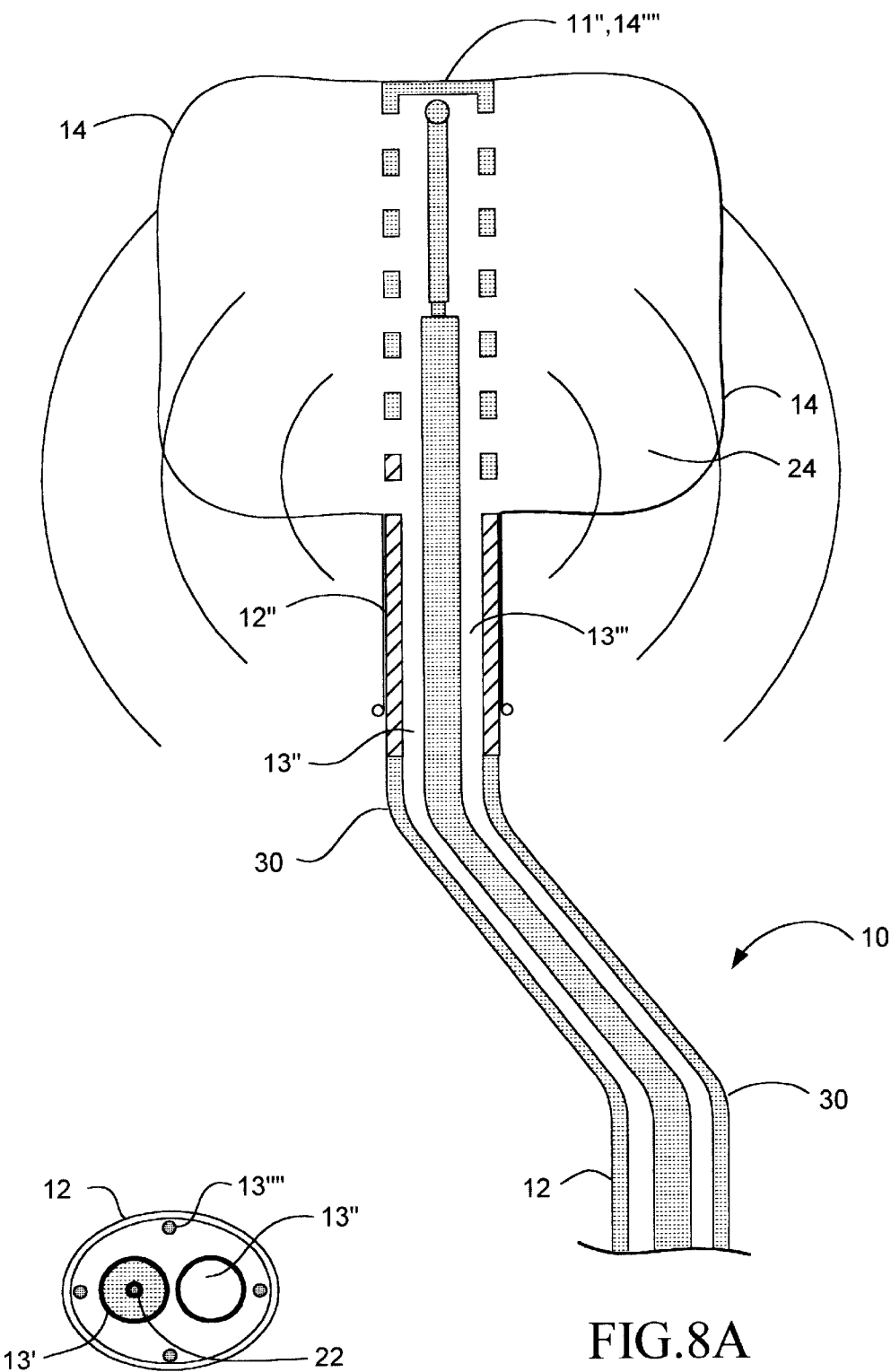
FIG. 8A is a lateral view of an embodiment of the apparatus having a bendable shaft.
FIG. 8B is a cross-sectional view of the elongated shaft of the embodiment from FIG. 8A.

Referring now to FIGS. 6a and 6b, in another embodiment, lumen 13' can be eccentric, or positioned off center, with respect to the center of shaft 12, but still be positioned on a center line 9 of shaft 12. Cooling media inflow lumen 13" can be similarly positioned on the same center line 9 as lumen 13'. Steering wire lumen 13"" is positioned off center line 9. Cooling out flow lumen 13'" fills the remainder of the space of the interior of shaft 12 not occupied by the other lumens. In this and related embodiments, shaft 12 can have a substantially oval or circular cross section. Cooling lumens 13" and 13'" in this embodiment can also be configured for absorption of microwaves. Specifically lumen 13'" and/or lumen 13" can be configured to surround 75% or more of the circumference of lumen 13' or coaxial cable 22.

Referring back to FIG. 3, in another embodiment, the delivery of microwave energy and heating of non target tissue can be prevented/reduced and the degree of microwave energy heating of a tissue site 18 can be selectively controlled by the use of a liquid microwave absorption media 24' that fills all or a portion of balloon 14. Specifically, microwave media 24' serves to absorb and reduce the power of microwaves radiating out from antenna 16. The degree of microwave absorption can be increased by: i) expanding the filled diameter of balloon 14 with microwave absorption media 24' or ii) adding microwave absorbing compounds 24" or compounds or particles 24" or compound containing solutions to media 24' to increase its microwave absorbing properties. Such compounds 24" are well known in the art and include carbon black, ferrites in the form of sintered iron and other metallic oxides having a cubic crystal structure and fullerenes or "Bucky Balls". Other microwave absorbable compounds 24" or particles 24" can be selected whose microwave absorbable properties increase with an increase in temperature or an increase in microwave power. Such compounds include the use of solids which undergo a partial or complete phase change to a liquid at a temperature within the operating range of temperatures of cooling media 24 or microwave absorbing media 24'. Such a temperature range include, but is not limited to a range of 0 to 70° C. with preferred embodiments of 30–50° C., 37–50° C. 37–60° C. 37–65° C. and 40–65° C. Such material includes, but is not limited to, one or more compounds found in margarine or butter and one or more fatty acids with melting points in the temperature range describe above. Additionally, the use of liposomes which contain microwave absorbing materials that are released upon rupture of the liposome wall with heat from microwave or other energy can also be employed.

Once added to balloon 14, all or a portion of microwave absorbing media 24' can be removed from balloon 14 and/or the concentration of absorbing compounds 24" can be reduced by aspirating balloon 14 using techniques known in the art. In various embodiments, absorption media 24' can include various aqueous solutions which can be used to suspend particles 24".

In various embodiments, absorbing media 24' can be the same as cooling media 24. Also, the degree of microwave absorption by filled balloon 14 can be determined through the use of microwave sensors 26 (well known in the art) positioned on or within the wall of balloon 14. This use of microwave absorbable compounds in balloon 14 represents a novel and distinct advantage in that delivered microwave power levels and the area of tissue heating can be controlled in vivo and more importantly can be titrated in vivo to achieve the desired tissue affect without injury to non-target tissue.

Alternative embodiments of the invention using a double jointed catheter 12 are shown in FIGS. 7a–7c and 8a–8b. Such joints 30, allow the movement of catheter 12 in two axises and serve to facilitate the introduction of apparatus 10 within the stomach using a transoral approach and the positioning and/or deployment of balloon 14 at a specific treatment site 18. Joints 30 can include swivel joints, articulated joints and other mechanical joints well known in the art. The movement about joints 30 can also be controlled by the use of pull wires using deflection mechanisms well known in the art.

The orientation of antenna 16 within the stomach can be obtained from either an incorporated or external medical imaging device such as an endoscope, video imaging camera, fiber optic viewing scope and the like. Antenna orientation within the stomach can also be ascertained via the use of an in vivo ultrasound transducer (positioned on the apparatus or in the esophagus as is known in the art) electronically coupled to an external ultrasound imaging device or through use of an external ultrasound transducer. In alternative embodiments, antenna orientation can also be obtained from a microwave receiver that is positioned on or within balloon 14. Depending upon the configuration of insulated coating antenna 16, the delivery of energy from antenna 16 can either be 360 omnidirectional or be directed out at in a beam arc 31' from 1 to 360°, with specific embodiments of 30, 45 60, 90, 120, 180 and 270°. For omnidirectional embodiments, the selection of a particular treatment site 18 can be made by positioning antenna 16 sufficiently close to the site such that the radiated power (dictated by the inverse square law known in the art) is high enough to cause the desired effect in the tissue (e.g. temperatures raised to range between 40–70° C. to cause collagen shrinkage). By similar application of the inverse square law and the control of the power supplied to antenna 16, the delivery of energy can be limited to the treatment site and kept below a threshold so as not to have a significant affect on tissue outside (e.g. at a set distance) from the tissue treatment site.

Referring back to FIGS. 2 and 3, apparatus 10 can also be configured for the delivery of a cooling media 24 to tissue site 18, or other portions of gastric mucosa 20" and stomach wall 20' as well as energy delivery device 16. Cooling media 24 can cool tissue site 18 and gastric mucosa 20' via convection, conduction or a combination thereof. Cooling media 24 can be delivered through lumen 13 to apertures 29 in elongated member 12 or balloon 14. The use of cooling preserves protects the mucosal layers 20' of the stomach and protects, or otherwise reduces the degree of cell damage in the vicinity of tissue site 18.

Suitable cooling media 24 include chilled fluids (such as cooled saline solutions) and gases and cryogenic solutions or gases (e.g. nitrogen or carbon dioxide). Alternatively, cooling media 24 can be contained within member 12 or balloon 14 and used to cool all or a portion of balloon 14 including external surface 14. In one embodiment, cooling media 24 can be a cryogen spray that is also used to inflate balloon 14. Cooling of a selected tissue site 18 is facilitated by assuring uniform contact of balloon surface 14' with gastric mucosa 20" including near or adjacent tissue site 18. In other embodiments cooling can be accomplished by use of a cooling device such as a thermoelectric cooling device (e.g. Peltier Effect Device) positioned on or within balloon 14 or otherwise coupled to balloon 14.

One or more sensors 26 may be coupled to balloon 14 and/or elongated member 12. Sensors 26 can include biomedical pressure transducers and LVDT's known in the art and can be used for measuring and/or assessing gastric distensibility, volume and motility. Similar techniques to esophageal manometry (a known procedure) may be used to make one or more of these assessments. This can include measurement of gastric motility by recording the pattern of pressure changes when the stomach is inflated to a prescribed volume.

Suitable pressure sensors 24 include strain gauge sensors including solid state (e.g. silicon based) sensors known in the art. Manometric measurements may be utilized to (i) make baseline measurements of gastric distensibility prior to treatment(s), (ii) assess the effectiveness of a given treatment in decreasing distensibility, (iii) determine the need for follow up treatments; and (iv) evaluate, determine and quantitate clinical endpoints. Such methods allow for a titrated/graduated delivery of therapy over varying periods of time to meet the varying needs of individual patients.

In other embodiments, sensors 26 can include temperature sensors for measuring the temperature of energy delivery devices 16, cooling media 24 and gastric tissue at or near tissue site 18. One or more temperature sensors 24 can be positioned or otherwise configured for temperature measurement of the gastric mucosa 20" and deeper tissue within stomach wall 20". Suitable temperature sensors 24 include thermocouples, thermistors, and IR detectors and the like.

In various embodiments, temperature sensors 24 can be configured and used for controlling the delivery of energy and/or cooling media to a selected tissue site 18 in order to optimize the generation of lesion /tissue contraction sites 21, and minimize thermal injury to tissue at or near tissue site 18 including gastric mucosa 20". Temperature sensor 24 and/or microwave power source 17 can be coupled to a feedback control system 28 known in the art (such as a PID-based system) to control, optimize or enhance the performance of one or more of these tasks. In various embodiments, the feedback control system 28 modifies or interrupts microwave power (or other energy source 17) if a selected temperature at the tissue surface or at a selected depth is exceeded. In related embodiments, energy delivery and tissue temperature can be controlled through the use of timed duty cycles (without feedback control) of cooling and power delivery. This includes prescribed periods of precooling, concurrent cooling and post cooling in addition to continuous cooling. The microwave power can be applied continuously or in a pulsed fashion. A database of cooling and heating is used to safely apply energy to the gastric wall without mucosal (or serosal) burning. The database can include tissue surface temperatures, tissue temperature depth and time profiles (e.g. rate of heating or cooling), and data (duration, frequency and amplitude) on the heating and cooling cycles.

It is advantageous for the physician to be able to monitor and be assured of the degree of contact of balloon 14 with gastric mucosa 20" before, during and after the delivery of energy to the tissue site. Accordingly in various embodiments, sensors 24 can include contact sensors known in the art. Sensors 24 can be coupled to an electronic monitoring system known in the art (which can also be the same as control system 28) to inform the physician of the degree of contact of balloon 14 with gastric mucosa 20". The combination of control system 28 and contact sensors 26 can also be used to regulate the delivery of energy to tissue site 18. Suitable contact sensors include strain gauges, impedance/conductivity sensors, optical sensors and ultrasound sensors.

In various embodiments, sensors 24 (including pressure, temperature, contact and microwave sensors) can be positioned on or within balloon 14 including external surface 14', internal surface 14" and also be embedded within the walls of balloon 14 or elongated member 12.

Sufficient energy is delivered to tissue site 18 to contract collagen tissue within the stomach wall 20' including the subserosal layers 20"" and/or initiate a wound healing response sufficient to cause fibroblasts and myofibroblasts to infiltrate into the site with subsequent deposition of a scar collagen matrix. These cells cause a contraction of tissue around lesion 21, decreasing its volume and distensibility (e.g. decreased flexibility, increased Young's modulus). This effect is further enhanced by the deposition of the scar collagen matrix. The net result is a tightening and reduction of the distensibility of the stomach wall tissue at or near lesion 21. A series of lesions 21 can be controllably placed in stomach wall 20' to controllably decrease the distensibility of all or any desired portion of stomach 20. In one embodiment, lesions 21 are positioned in a circumferential manner in stomach wall 20' so as to produce a circumferential wound healing response in stomach wall 20' and fibroblastic reduction in stomach diameter along with an accompanying decrease in distensibility. This decreased distensibility increases the tension in stomach wall 20' with a concomitant increase in the stimulation of stomach wall tension receptors 27 for a given volumetric increase of the stomach due to the consumption of food. The increased stimulation of stomach wall tension receptors 27 in turn may serve to produce neurological perception of a full stomach feeling for a smaller volume of consumed food. In various embodiments, the response or output from wall tension receptors 27 can be measured using electrogastrographic methods (including evoked response methods) and devices (such as the Digitrapper® EGG manufactured by the Medtronic Synectics, Stockholm Sweden) and used to assess the effectiveness of individual treatments and establish clinical endpoints.

The ability to predict the depth and extent of subsurface tissue heating may be useful for improving the performance of the apparatus in one or more embodiments of the present invention. Appendix 1 discloses a tissue interaction model that describes the interaction of heating and cooling in general descriptive terms. Multiple patterns of subsurface tissue heating are created that can be observed histologically and morphologically. Radio frequency or microwave energy are two of the more frequently used energy sources but others are equally applicable.

The heating of viable tissue is mainly determined by the duration and timing of surface convection cooling with the delivery of electromagnetic energy into the subjacent tissue. Patterns of tissue heating are predicted with four different permutations of cooling and power. These permutations and patterns of tissue heating are described in reference to the following definitions. With the aid of a spread sheet disclosed in Appendix 2, the model can predict depth and temperature of tissue heating at specific settings of cooling and microwave power.

Figure 10:
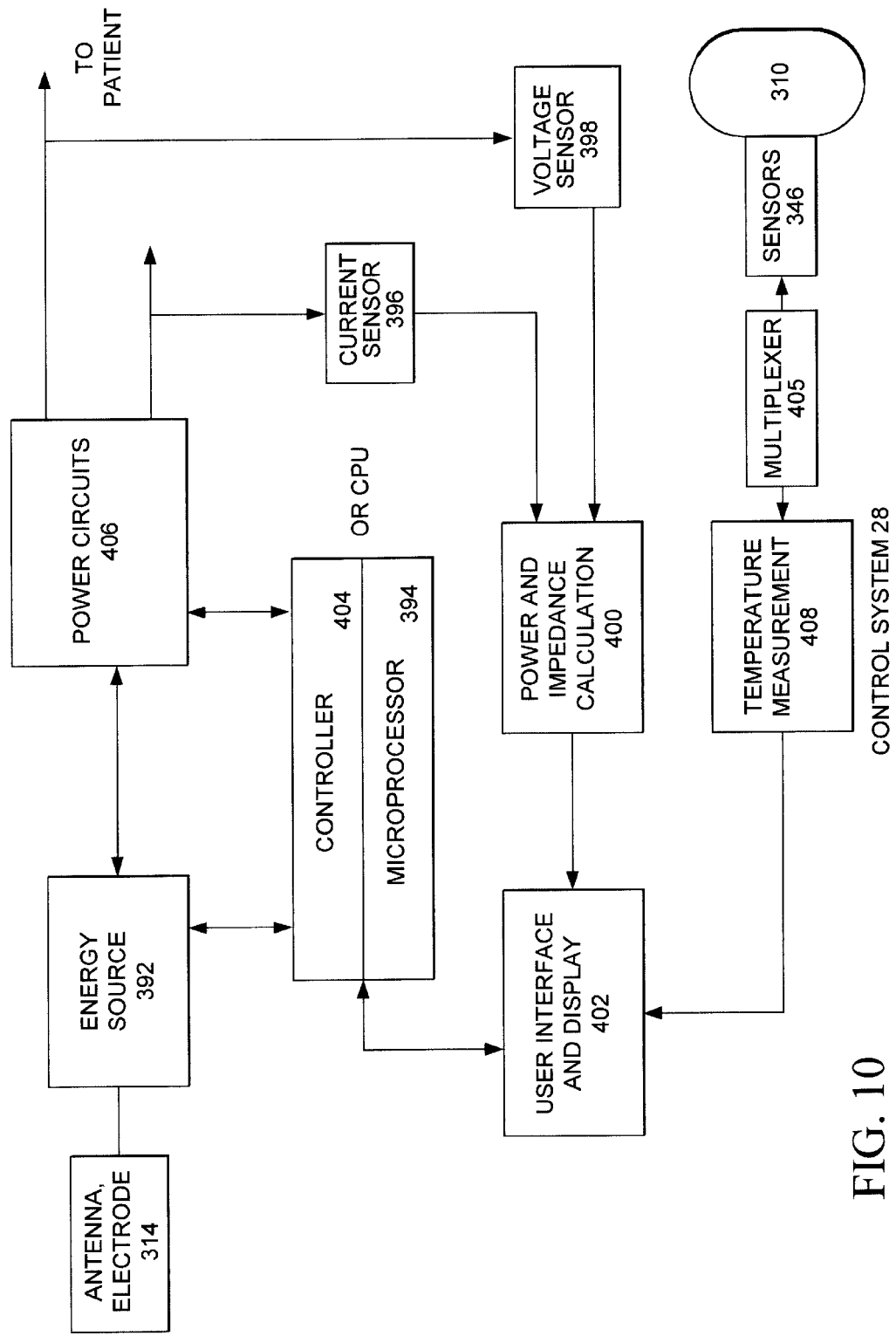
FIG. 10 depicts a block diagram of the feed back control system that can be used with the pelvic treatment apparatus.

In an embodiment, elements of stomach treatment apparatus 10 can be coupled to an open or closed loop feedback control system 28, also called feedback resources 28. Referring now to FIG. 10, an open or closed loop feedback control system 28 couples sensor 346 to energy source 392. In this embodiment, energy delivery device 314 is one or more microwave antennas 314. The temperature of the tissue, or of microwave antenna 314, is monitored, and the output power of energy source 392 adjusted accordingly. The physician can, if desired, override the closed or open loop control system 28. Logic resources 394, also called microprocessor 394, can be included and incorporated in the closed or open loop system to switch power on and off, as well as modulate the power. Closed loop feedback control system 28 utilizes microprocessor 394 to serve as a controller, monitor the temperature or tissue contact force, adjust the microwave power, analyze the result, refeed the result, and then modulate the power or fluid flow rate.

With the use of sensor 346 and feedback control system 28, tissue adjacent to microwave antenna 314 can be maintained at a desired temperature for a selected period of time without causing a shut down of the power circuit to electrode 314 due to the development of excessive electrical impedance at electrode 314 or adjacent tissue as is discussed herein. Each microwave antenna 314 is connected to resources that generate an independent output. The output maintains a selected energy at microwave antenna 314 for a selected length of time.

Current delivered through microwave antenna 314 is measured by current sensor 396. Voltage is measured by voltage sensor 398. Impedance and power are then calculated at power and impedance calculation device 400. These values can then be displayed at a user interface and display 402. Signals representative of power and impedance values are received by a controller 404. A control signal is generated by controller 404 that is proportional to the difference between an actual measured value, and a desired value. The control signal is used by power circuits 406 to adjust the power output an appropriate amount in order to maintain the desired power delivered at respective microwave antennas 314.

In a similar manner, temperatures detected at sensor 346 provide feedback for maintaining a selected power. Temperature at sensor 346 is used as a safety means to interrupt the delivery of power when maximum pre-set temperatures are exceeded. The actual temperatures are measured at temperature measurement device 408, and the temperatures are displayed at user interface and display 402. A control signal is generated by controller 404 that is proportional to the difference between an actual measured temperature and a desired temperature. The control signal is used by power circuits 406 to adjust the power output an appropriate amount in order to maintain the desired temperature delivered at the sensor 346. A multiplexer 405 can be included to measure current, voltage and temperature, at the sensor 346, and energy can be delivered to microwave antenna 314 in continuous or pulsed fashion.

In various embodiments, user interface and display 402 can include operator controls. Controller 404 can be a digital or analog controller, or a digital computer with embedded software (e.g. on a ROM chip) loadable software (e.g. by disc, CD or other readable storage media), or downloadable software from a distributed computer network (e.g. the internet). When controller 404 is a computer it can include a central processing unit or CPU electronically coupled to various components of control system 28 through a system bus. This computer system can include a keyboard, a disk drive, or other non-volatile memory systems, a display, and other peripherals, as are known in the art. A program memory, data memory, RAM and ROM can also be coupled to the bus. Also, controller 404 can be coupled to imaging systems including, but not limited to, ultrasound, CT scanners (including fast CT scanners), X-ray, MRI, mammographic X-ray and the like. Further, direct visualization and tactile imaging can also be utilized.

The output of current sensor 396 and voltage sensor 398 are used by controller 404 to maintain a selected power level at each microwave antenna 314. The amount of microwave energy delivered controls the amount of power. A profile of the power delivered to antenna 314 can be incorporated in controller 404 and a preset amount of energy to be delivered may also be profiled.

Circuitry, software and feedback to controller 404 result in process control, the maintenance of the selected power (microwave or other) setting which is independent of changes in voltage or current, and is used to change the following process variables: (i) the selected microwave power setting, (ii) the duty cycle (e.g., on-off time), (iii) standing wave ratio; and, (iv) fluid delivery, including flow rate and pressure. These process variables are controlled and varied, while maintaining the desired delivery of power independent of changes in voltage or current, based on temperatures monitored at sensor 346. Similar process controls can be used to monitor tissue temperature to produce collagen contraction or initiate a wound healing response at a selectable tissue depth at tissue site 416. In related embodiments control resources 28 can be used to monitor and control the distensiblity and volume of the stomach by controlling energy delivery at tissue site 416 and monitoring the distensibility of tissue site/stomach 416 using one or more pressure or force or sensors 346 distributed over the expandable member 310.

Figure 11:
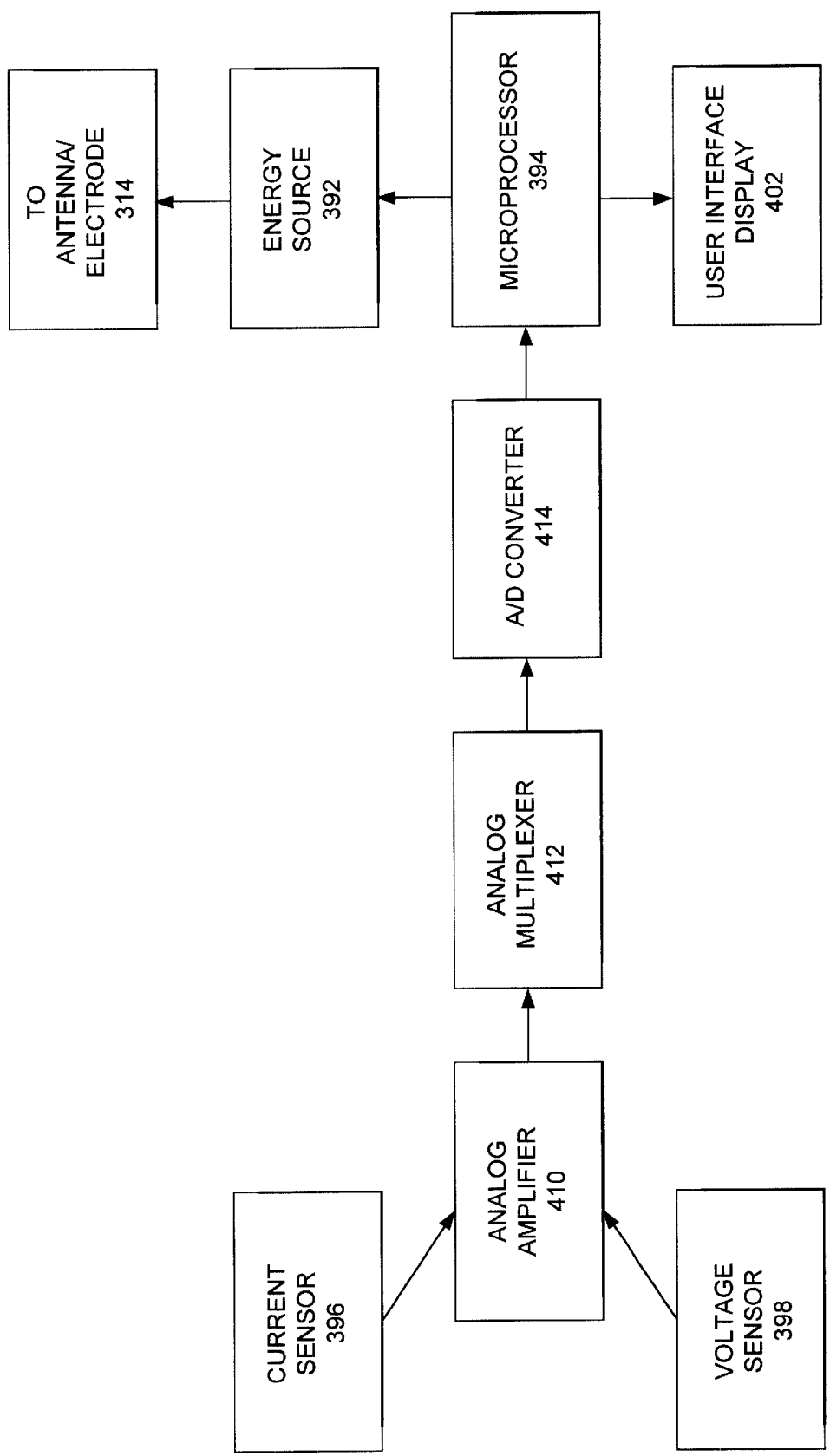
FIG. 11 depicts a block diagram of an analog amplifier, analog multiplexer and microprocessor used with the feedback control system of FIG. 10.

Referring now to FIG. 11, current sensor 396 and voltage sensor 398 are connected to the input of an analog amplifier 410. Analog amplifier 410 can be a conventional differential amplifier circuit for use with sensor 346. The output of analog amplifier 410 is sequentially connected by an analog multiplexer 412 to the input of A/D converter 414. The output of analog amplifier 410 is a voltage, which represents the respective sensed temperatures. Digitized amplifier output voltages are supplied by A/D converter 414 to microprocessor 394. Microprocessor 394 may be a type 68HCII available from Motorola. However, it will be appreciated that any suitable microprocessor or general purpose digital or analog computer can be used to calculate impedance or temperature.

Microprocessor 394 sequentially receives and stores digital representations of impedance and temperature. Each digital value received by microprocessor 394 corresponds to different temperatures and impedances.

Calculated power and impedance values can be indicated on user interface and display 402. Alternatively, or in addition to the numerical indication of power or impedance, calculated impedance and power values can be compared by microprocessor 394 to power and impedance limits. When the values exceed or fall below predetermined power or impedance values, a warning can be given on user interface and display 402, and additionally, the delivery of microwave energy can be reduced, modified or interrupted. A control signal from microprocessor 394 can modify the power level supplied by energy source 392.

Figure 12:
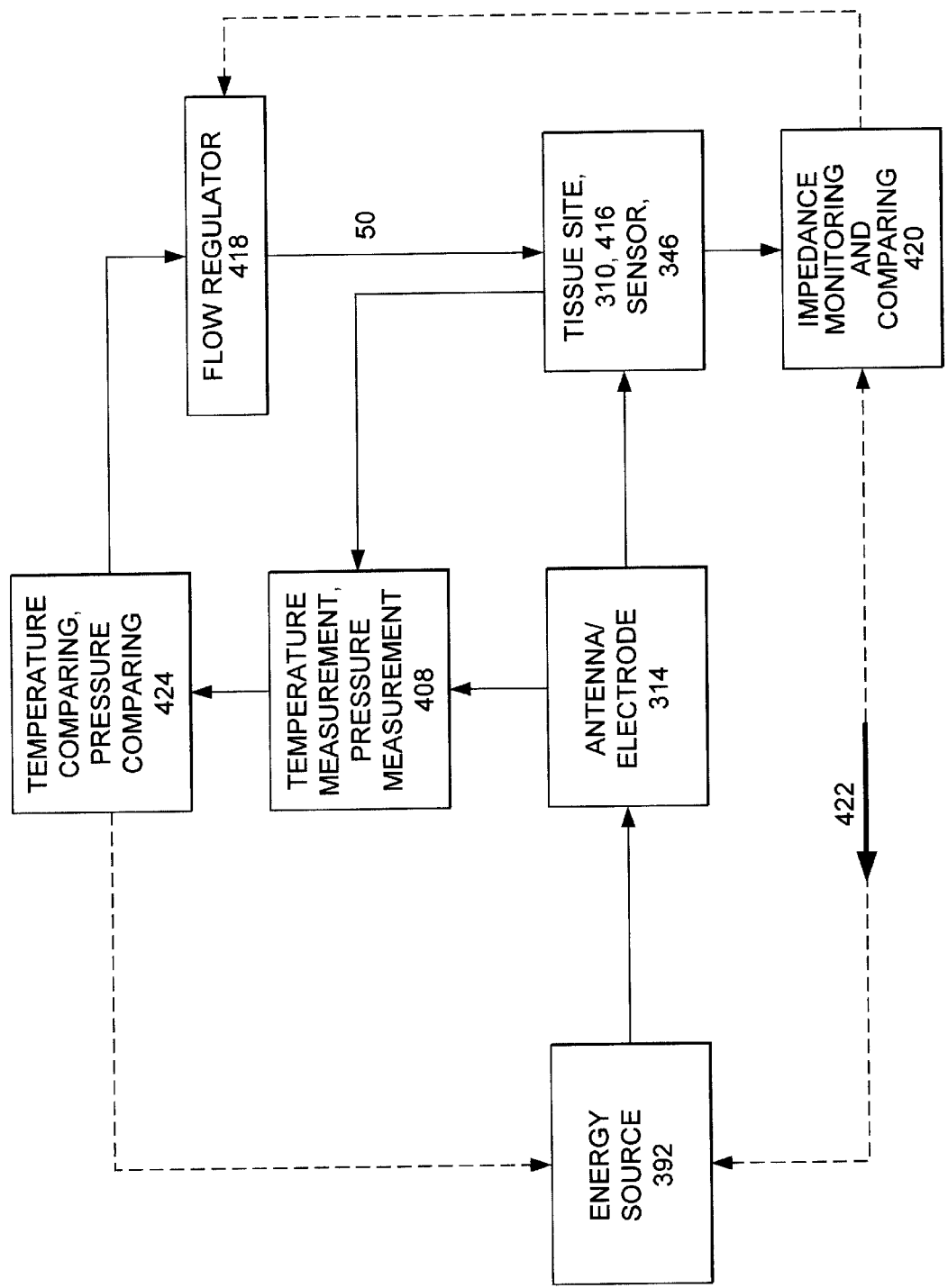
FIG. 12 depicts a block diagram of the operations performed in the feedback control system depicted in FIG. 11.

FIG. 12 illustrates a block diagram of a temperature and impedance feedback system that can be used to control the delivery of energy to tissue site 416 by energy source 392 and the delivery of cooling medium 50 to electrode 314 and/or tissue site 416 by flow regulator 418. Energy is delivered to microwave antenna 314 by energy source 392, and applied to tissue site 416. A monitor 420 (also called impedance monitoring device 420) ascertains tissue impedance, based on the energy delivered to tissue, and compares the measured impedance value to a set value. If measured impedance is within acceptable limits, energy continues to be applied to the tissue. However if the measured impedance exceeds the set value, a disabling signal 422 is transmitted to energy source 392, ceasing further delivery of energy to microwave antenna 314. The use of impedance monitoring with control system 28 provides a controlled delivery of energy to tissue site 416 (also called mucosal layer 416) and underlying cervical soft tissue structure which reduces, and even eliminates, cell necrosis and other thermal damage to mucosal layer 416. Impedance monitoring device 420 is also used to monitor other conditions and parameters including, but not limited to, presence of an open circuit, short circuit; or if the current/energy delivery to the tissue has exceeded a predetermined time threshold. Such conditions may indicate a problem with apparatus 10. Open circuits are detected when impedance falls below a set value, while short circuits and exceeded power delivery times are detected when impedance exceeds a set value.

The control of cooling medium 50 to electrode 314 and/or tissue site 416 is done in the following manner. During the application of energy, temperature measurement device 408 measures the temperature of tissue site 416 and/or microwave antenna 314. A comparator 424 receives a signal representative of the measured temperature and compares this value to a pre-set signal representative of the desired temperature. If the measured temperature has not exceeded the desired temperature, comparator 424 sends a signal to flow regulator 418 to maintain the cooling solution flow rate at its existing level. However, if the tissue temperature is too high, comparator 424 sends a signal to a flow regulator 418 (connected to an electronically controlled micropump, not shown) representing a need for an increased cooling solution flow rate.

The foregoing description of a preferred embodiment of the invention has been presented for purposes of illustration and description. It is not intended to be exhaustive or to limit the invention to the precise forms disclosed. Obviously, many modifications, variations and different combinations of embodiments will be apparent to practitioners skilled in this art. Also, elements from one embodiment can be recombined with one or more other embodiments. For example, in various other embodiments, the invention may also be applicable to the non-invasive management of gastroesophageal reflux, intestinal stomas and other gastrointestinal related disorders and pathologies and sleep apnea. Sequential treatments for sleep apnea with non invasive contraction of the soft palate and tongue will provide a more precise correction than a single surgery. Non-invasive contraction of an intestinal viscus should significantly benefit the creation of continent ileostomies for patients who have undergone a total colectomy for ulcerative colitis or Crohn's disease. Patients that require resection of the rectosigmoid colon may avoid a permanent colostomy with a pull through insertion onto the anal vault. Reduction of small bowel absorption may provide another means of weight control other than non-invasive gastroptyxis. Furthermore, this specification is not intended to be exhaustive or to limit the invention to the precise forms disclosed.

Appendix 1 Tissue Interaction Model

Figure 9:
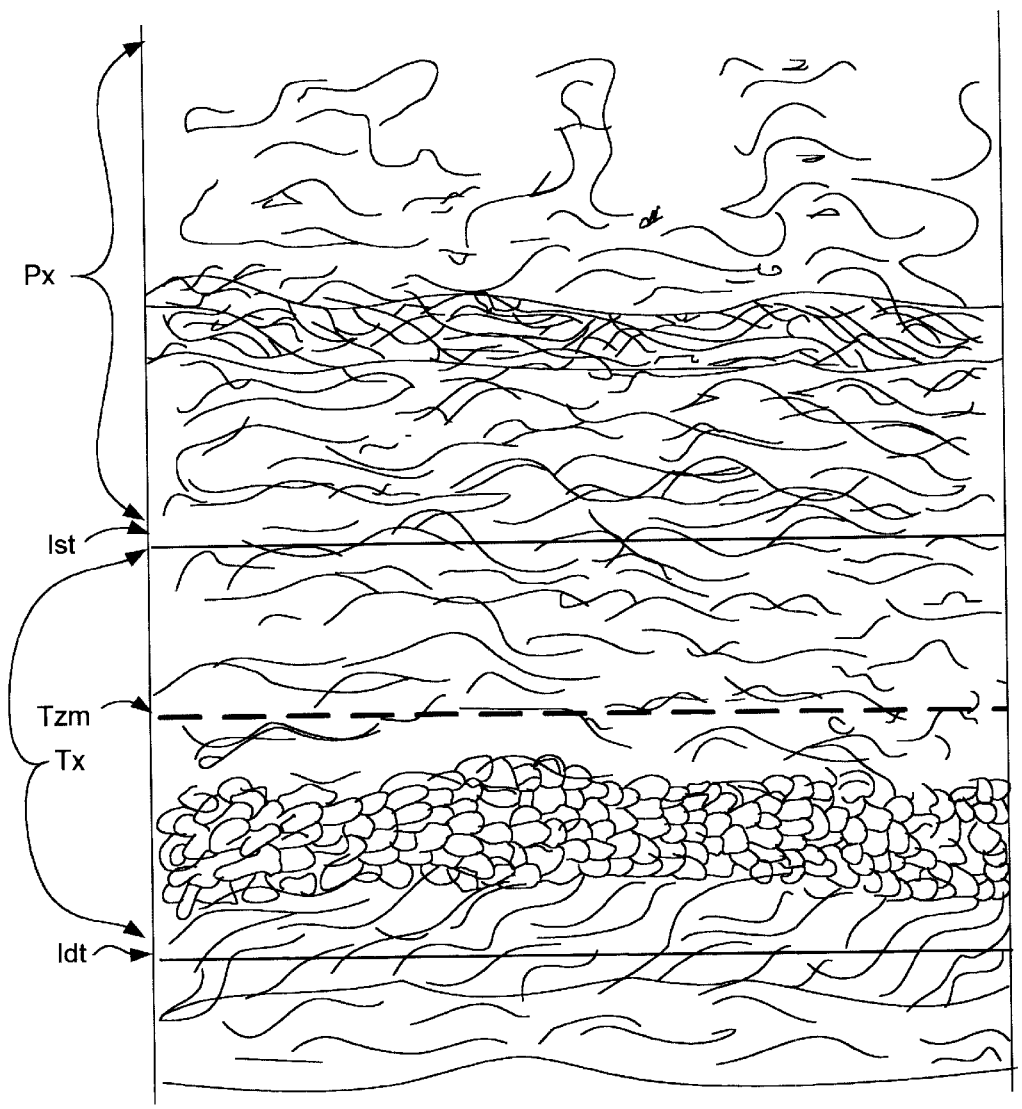
FIG. 9 is a lateral view of the stomach wall illustrating the various parameter/zones of the tissue interaction model described in an embodiment of the invention.

Model Definitions: Listed below are the definitions of various parameters used in the model. These parameters are also illustrated in FIG. 9.

1. TGP: Total Grid Power. This is the power (watts) that is delivered by the RF generator or the microwave magnetron to the RF electrode or microwave antenna.
2. TGE: Total Grid Energy is the amount of energy (Joules) that is delivered by the power source in a specific period of time to the RF electrode or microwave antenna.
3. CC: Convection cooling. This is the heat loss from the tissue surface due to forced convective flow of a cooling solution over the tissue. Convection cooling is measured as in units of joules/secs and is dependent upon the flow rate of the cooling fluid, the temperature gradient between the tissue and the cooling solutions
4. Pcd: Precool Duration.
5. Dt: Duration of treatment.
6. Tf: Tissue fluence. This is defined as the amount of energy delivered to the tissue and is the net product of total grid energy minus surface convection cooling.
7. Px: Protected Region of the tissue surface
8. Tx: Treatment zone. This is the zone that is subjacent to the protected region
9. Tzt: Treatment Zone Thickness. This the is the thickness measured between the superficial and the deep tissue interfaces.
10. Tzm: Treatment Zone Median is the line that horizontally bisects the treatment zone
11. Ist: Superficial tissue Interface. This is the most superficial level of the treatment zone that is immediately subjacent to the protected region.
12. Idt: Deep Tissue Interface. This is the deepest level of the treatment zone that is in contact with subjacent soft tissue
13. D%: Percent Denaturation. This represents the relative amount of denatured matrix within the treatment zone.

Permutations of Power and Cooling with Predicted Patterns of Tissue Heating

1. Pcd- and Tge-=Px$^-$- and Tx-. The effect upon the Px is canceled between an increased duration of cooling and an increase in grid power. There will be little or no movement of superficial interface (Ist). The thickness of the treatment zone (Tz) is increased with a lowering of the deep interface (Idt). The treatment zone median (Tzm) is lowered with an increase in the percent denaturation (D%). A deep pattern of densely denatured matrix of the submucosa and muscle is predicted with preservation of the mucosa. The pattern will be evident on H&E stain.
2. Pcd$^-$ and Tge-=Px$^-$ and Tx-. Acts in concert to decrease the protected zone (Px). The superficial interface (Ist) is raised and the deep interface (Idt) is deepened. The thickness of the treatment zone (Tz) is increased and the treatment zone median is deepened. The percent denaturation (D%) of the matrix is increased. The probability of mucosal necrosis is increased. It is predicted that the matrix will be densely compacted and denatured throughout the entire thickness of the submucosa. The pattern will be evident on H&E stain.
3. Pcd- and Tge$^-$=Px- and Tx$^-$. Acts in concert to increase the preserved region (Px) and decrease the treatment zone (Tx). The superficial interface is (Tis) is lowered and the deep interface (Tid) is raised. The treatment zone thickness (Tzt) is narrowed and the percent denaturation (D%) is decreased. The treatment zone median (Tzm) is unchanged. It is predicted that the mid submucosal matrix will be contracted but minimal denaturation will be visible with an H&E stain. The mucosal and the lamina propria will be preserved. This combination of cooling and power may produce an optimal tissue heating pattern for gastroptyxis.
4. Pcd$^-$ and Tge$^-$=Px- and Tx$^-$. Acts to cancel the effect on the preserved region (Px) and the treatment zone (Tx). The superficial interface (Ist) will be raised slightly and the deep interface (Idt) will be raised a greater amount. The treatment zone thickness (Tzt) will be narrowed and the treatment zone median (Tzm) will be raised. The percent denaturation (D%) will be decreased. It is predicted that a more superficial pattern of heating in the submucosa will occur with preservation of the fundal mucosa. Minimal denaturation of the treatment zone will be evident on an H&E stain.

The Effect of Heating Duration. Although the laser literature has supported the concept of millisecond pulsing, the continuous application of microwave energy has been described for the "non invasive" treatment of benign prostatic hypertrophy. With RF power, pulsed and continuous modes of application have been evaluated. Shorter durations with pulsing may provide advantages for dynamic applications but may not provide enough time for uniform thermal conduction within a treatment zone. Continuous applications of RF power may not provide the same degree of control in a dynamic application, but may provide a more uniform pattern of heating in a treatment zone. Overall, the shortest duration of power will be limited by the need to evenly heat tissue by thermal conduction. The longest duration of power will be limited by the thermal conductivity of tissue in combination with convection losses from the mucosal surface and convection losses from subjacent vascular structures.

Electrode configuration and Phase transitions: Changes in electrode geometry will also modify the pattern of tissue heating at both treatment interfaces. In comparison to a monopolar array, a bipolar or hybrid polar array will decrease the depth of the deep interface and increase the percent denaturation for a specific setting of grid power. Regardless of the electrode geometry, a phase transition with freezing of the tissue surface will deepen the level of the superficial interface. With a bipolar array, the deep interface is raised and the superficial interface is deepened with freezing of the tissue surface. As a result, a narrow treatment zone with compaction of the matrix will be created with bipolar electrodes.

Appendix 2 Mathlab Spread Sheet For Microwave Heating

From preliminary bench testing, a spread sheet of predicted temperatures within tissue has been created. The spread accounts for variations in tissue depth and microwave power. Additional variation in temperature will be observed with different tissues and different device geometries.

Tissue Temperature Predictor — Table cells show degrees C.

Rows are for time in seconds.
Columns are for depth in mm.

| | |
|---|---|
| 12.0 | Set absorbed microwave power in watts/cm2. |
| 50.0 | Set time in seconds for when to turn on microwaves. |
| 90.0 | Set time in seconds for when to turn off microwaves. |

| mm | 0.0 | 1.0 | 2.0 | 3.0 | 4.0 | 5.0 | 6.0 | 7.0 |
|---|---|---|---|---|---|---|---|---|
| | 0.0 | 37.0 | 37.0 | 37.0 | 37.0 | 37.0 | 37.0 | 37.0 |
| | 0.0 | 35.3 | 37.0 | 37.0 | 37.0 | 37.0 | 37.0 | 37.0 |
| | 0.0 | 33.8 | 36.9 | 37.0 | 37.0 | 37.0 | 37.0 | 37.0 |
| | 0.0 | 32.4 | 36.7 | 37.0 | 37.0 | 37.0 | 37.0 | 37.0 |
| | 0.0 | 31.2 | 36.5 | 37.0 | 37.0 | 37.0 | 37.0 | 37.0 |
| | 0.0 | 30.0 | 36.2 | 36.9 | 37.0 | 37.0 | 37.0 | 37.0 |
| | 0.0 | 28.9 | 36.0 | 36.9 | 37.0 | 37.0 | 37.0 | 37.0 |
| | 0.0 | 27.9 | 35.7 | 36.9 | 37.0 | 37.0 | 37.0 | 37.0 |
| | 0.0 | 27.0 | 35.3 | 36.8 | 37.0 | 37.0 | 37.0 | 37.0 |
| | 0.0 | 26.2 | 35.0 | 36.7 | 37.0 | 37.0 | 37.0 | 37.0 |
| | 0.0 | 25.4 | 34.7 | 36.7 | 37.0 | 37.0 | 37.0 | 37.0 |
| | 0.0 | 24.7 | 34.3 | 36.6 | 36.9 | 37.0 | 37.0 | 37.0 |
| | 0.0 | 24.0 | 33.9 | 36.5 | 36.9 | 37.0 | 37.0 | 37.0 |
| | 0.0 | 23.4 | 33.6 | 36.4 | 36.9 | 37.0 | 37.0 | 37.0 |

Do not change values below this line

| | | | | | | | | |
|---|---|---|---|---|---|---|---|---|
| Depth in mm | 0.0 | 1.0 | 2.0 | 3.0 | 4.0 | 5.0 | 6.0 | 7.0 |
| Deg C rise/(joule*cm2) | | 0.1077 | 0.0980 | 0.0891 | 0.0811 | 0.0738 | 0.0672 | 0.0611 |
| Deg C rise | | 1.2918 | 1.1755 | 1.0697 | 0.9735 | 0.8859 | 0.8061 | 0.7336 |
| Time interval, sec | | 0.5 | | | | | | |
| | | 0.9129 | 0.0426 | 0.0010 Per Matlab | | | | |
| Thermal coefficients | | 0.9100 | 0.0440 | 0.0010 Used | | 1.0000 | | |

What is claimed is:

1. An apparatus to modify a stomach wall comprising:
an elongated member including at least one lumen;
a deployable member coupled to the elongated member, the deployable member configured to be advanceable and removable from the stomach in a non-deployed state and sized to be positioned in the stomach in a deployed state to engage at least portions of the stomach wall, the deployable member further configured to contain a fluidic media, at least a portion of a deployable member wall configured to be cooled by the fluidic media, at least a portion of the deployable member having a contour in the deployed state approximating at least a portion of a stomach interior, wherein at least a portion of the deployable member include one of a microwave absorbable material or a microwave absorbable material with a variable microwave absorption;
a microwave antenna movably positioned in the deployable member so as to control a microwave field strength vector in relation to the antenna, the microwave antenna being configured to be coupled to a microwave energy source and deliver microwave energy to a selectable tissue site in the stomach wall while minimizing thermal injury to one of a mucosal or a submucosal layer; and
a cable member coupled to the microwave antenna, the cable member configured to be advanceable within the elongated member.

2. The apparatus of claim 1, wherein the contour includes a first radius of curvature and a second radius of curvature, the second radius of curvature being greater than the first radius of curvature and at least a portion of the first curvature being substantially parallel to at least a portion of the second curvature.

3. The apparatus of claim 2, wherein the first radius of curvature approximates a stomach lesser curvature and the second radius of curvature approximates a stomach greater curvature.

4. The apparatus of claim 1, wherein the expansion device deployed has a contour approximating at least one of a fundus, an antrum, a stomach corpus or a pyloric region.

5. The apparatus of claim 1, wherein at least portion of the elongated member is formed of one of a microwave absorbable material or a microwave absorbable material with a variable microwave absorption.

6. The apparatus of claim 5, wherein the microwave absorption varies with respect to at least one of a temperature or an emitted microwave power.

7. The apparatus of claim 1, wherein the at least one expansion member or the elongated member includes at least one aperture.

8. The apparatus of claim 7, wherein the at least one aperture is fluidically coupled with the at least one lumen.

9. The apparatus of claim 1, wherein the fluidic medium contains at least one of a cooling fluid, a cooled fluid, a microwave absorbing solution, a microwave absorbing particle or a microwave absorbing solution with a variable microwave absorption.

10. The apparatus of claim 9, wherein the microwave absorbing solution has a microwave absorption that varies with one of a solution temperature or an emitted microwave power.

11. The apparatus of claim 1, wherein the antenna further comprises a plurality of radiating elements.

12. The apparatus of claim 11, wherein the plurality of radiating elements comprise an array of radiating elements or an array of radiating elements distributed along a beam axis of symmetry.

13. The apparatus of claim 1, further comprising: a microwave absorbable sheath member slidably positioned over the microwave antenna.

14. The apparatus of claim 13, wherein the sheath member is configured to control one of a radiating length of the microwave antenna, an emitted microwave radiation power level, or a microwave field strength.

15. The apparatus of claim 1, wherein the antenna has a directionally selectable microwave beam.

16. The apparatus of claim 15, wherein the antenna has a selectable beam arc in the range from 1 to 360°.

17. The apparatus of claim 1, wherein the position of the microwave absorbable material is configured to produce a directional microwave beam.

18. The apparatus of claim 17, wherein the beam has a beam arc in the range from 1 to 360°.

19. The apparatus of claim 1, wherein the antenna is configured to radiate microwave energy at a frequency range selected from the group consisting of about 915 MHz to about 2.45 GHz and about 1250 MHz to about 1350 MHz.

20. The apparatus of claim 1, wherein the antenna comprises: a first and a second dipole element.

21. The apparatus of claim 20, wherein one of the first dipole element has a cylindrical shape and the second dipole element has one of a cylindrical shape or a cylindrical ball-tipped shape.

22. The apparatus of claim 20 wherein one of a first dipole element length or a second dipole element length is substantially nonequivalent to one quarter of a selected microwave wavelength.

23. The apparatus of claim 22 wherein the microwave antenna has a slow wave structure.

24. The apparatus of claim 1, wherein an expansion member parameter is configured to yield an expansion member compliance less than the stomach wall.

25. The apparatus of claim 24, wherein the expansion member parameter includes at least one of an expansion member wall thickness, an expansion member shape, an expansion member size or an expansion member material.

26. The apparatus of claim 24, wherein the expansion member is configured to conform to at least a portion of the stomach wall when the expansion member is in the deployed state.

27. The apparatus of claim 24, wherein the expansion member is configured to uniformly contact the stomach wall including a stomach wall crevice.

28. The apparatus of claim 1, further comprising:
an inner elongated member disposed within the elongated member, the inner member including a lumen.

29. The apparatus of claim 28, wherein the inner member is advanceable within the elongated member.

30. The apparatus of claim 28, wherein at least portions of the inner member include a fluid lumen, a reinforcing braid, a radiopaque marker or an echogenic marker.

31. The apparatus of claim 28, wherein at least a portion of the inner member include one of a microwave absorbable material or a microwave absorbable material with a variable microwave absorption.

32. The apparatus of claim 28, wherein the inner member is slidably advanceable over at least portions of the antenna.

33. The apparatus of claim 28, wherein at least one of the elongated member or the inner member is deflectable.

34. The apparatus of claim 33, wherein at least one of the elongated member or the inner member has an articulated portion.

35. The apparatus of claim 33, wherein at least one of the elongated member or the inner member is coupled to a deflection mechanism.

36. The apparatus of claim 1, further comprising:
a sensor coupled to one of the expansion member or the elongated member.

37. The apparatus of claim 36, wherein the sensor is one of a microwave sensor, a thermal sensor, an ultrasound transducer, an optical sensor, a pressure sensor, a force sensor or a contact sensor.

38. The apparatus of claim 36, wherein the sensor is a contact sensor configured to facilitate positioning the deployable member adjacent a selectable portion of the stomach wall.

39. The apparatus of claim 36, wherein the sensor comprises a first sensor coupled to the deployable member and second sensor coupled to the microwave antenna.

40. The apparatus of claim 36, wherein the first and second sensors are configured to monitor one of a microwave antenna position, a microwave beam direction or a microwave field strength.

41. The apparatus of claim 36, further comprising feedback control resources coupled to at least one of the sensor, the antenna, microwave power source coupled to the antenna or a fluid delivery device coupled to the elongated member.

42. The apparatus of claim 41, wherein the feedback control resources are configured to reduce one of an expansion member surface temperature or an expansion member tissue interface temperature.

43. The apparatus of claim 41, wherein the feedback control resources are configured to minimize thermal injury to one of a mucosa or submucosa in proximity to the expansion member.

44. The apparatus of claim 41, wherein one of the feedback control resources, the antenna or an antenna beam is configured to cause collagen contraction of a selectable depth of the stomach wall.

45. The apparatus of claim 41, wherein one of the feedback control resources, the antenna or an antenna beam is configured to initiate a wound healing response of a selectable portion of the stomach.

46. The apparatus of claim 45, wherein the wound healing response is of a selectable circumferential portion of the stomach.

47. The apparatus of claim 45, wherein the wound healing response is of a selectable portion of the stomach w all.

48. The apparatus of claim 41, wherein the feedback control resources are configured to monitor and reduce a distensibility of at least a portion of the stomach.

49. The apparatus of claim 41, wherein the feedback control resources are configured to reduce a volume of at least a portion of the stomach.

50. The apparatus of claim 41, wherein the feedback control resources are configured to control one of an input microwave power to the antenna, an antenna emitted microwave power, an antenna microwave field strength, or a fluid media flow to the expansion member.

51. An apparatus to modify a stomach wall comprising:
an elongated member with at least one lumen that includes a fluid lumen and a cable member lumen, wherein the fluid lumen is positioned in a substantially surrounding relationship to the cable lumen;
a deployable member coupled to the elongated member, the deployable member configured to be advanceable and removable from the stomach in a non-deployed state and sized to be positioned in the stomach in a deployed state to engage at least portions of the stomach wall, the deployable member further configured to contain a fluidic media, at least a portion of a deployable member wall configured to be cooled by the fluidic media, the deployable member having a contour in the deployed state approximating at least a portion of a stomach interior;

a microwave antenna movably positioned in the deployable member so as to control a microwave field strength vector in relation to the antenna, the microwave antenna being configured to be coupled to a microwave energy source and deliver microwave energy to a selectable tissue site in the stomach wall while minimizing thermal injury to one of a mucosal or a submucosal layer; and a cable member coupled to the microwave antenna, the cable member configured to be advanceable within the elongated member.

52. The apparatus of claim 51, wherein the fluid lumen includes a first fluid lumen and second fluid lumen.

53. The apparatus of claim 51, wherein the fluid lumen is positioned relative to the cable lumen to increase heat exchange between a cooling fluid disposed in the fluid lumen and the cable lumen.

54. The apparatus of claim 51, wherein the fluid lumen is positioned relative to the cable lumen to increase absorption of microwaves radiating from the cable lumen by a microwave absorbing media disposed in the fluid lumen.

55. The apparatus of claim 51, wherein the fluid lumen has one of a semi-circular shape, a kidney shape or a crescent shape.

56. The apparatus of claim 51, wherein the fluid lumen and the cable lumen have a substantially common locus.

57. An apparatus to modify a stomach wall comprising:
an elongated member with at least one lumen;
a deployable member coupled to the elongated member, the deployable member configured to be advanceable and removable from the stomach in a non-deployed state and sized to be positioned in the stomach in a deployed state to engage at least portions of the stomach wall, the deployable member further configured to contain a fluidic media, at least a portion of a deployable member wall configured to be cooled by the fluidic media, at least a portion of the deployable member having a contour in the deployed state approximating at least a portion of a stomach interior;
a microwave antenna movably positioned in the deployable member so as to control a microwave field strength vector in relation to the antenna, the microwave antenna being configured to be coupled to a microwave energy source and deliver microwave energy to a selectable tissue site in the stomach wall while minimizing thermal injury to one of a mucosal or a submucosal layer, wherein the antenna is constructed from a portion of a coaxial cable; and
a cable member coupled to the microwave antenna, the cable member configured to be advanceable within the elongated member.

58. The apparatus of claim 57, wherein the antenna comprises a slotted radiating portion of the coaxial cable.

59. The apparatus of claim 57, wherein the antenna further comprises:
an inner conductor;
an inner insulation layer substantially surrounding the inner conductor;
an outer conductor substantially surrounding the inner insulation; and
an outer insulation layer substantially surrounding the outer conductor.

60. The apparatus of claim 59, wherein the inner insulation layer comprises a plurality of insulation segments longitudinally distributed over the inner conductor with a gap between each insulation segment.

61. An apparatus to modify a stomach wall comprising:
an elongated member including at least one lumen;
a deployable member coupled to the elongated member, the deployable member configured to be advanceable and removable from the stomach in a non-deployed state and sized to be positioned in the stomach in a deployed state to engage at least portions of the stomach wall, the deployable member further configured to contain a fluidic media, at least a portion of a deployable member wall configured to be cooled by the fluidic media, at least a portion of the deployable member having a contour in the deployed state approximating at least a portion of a stomach interior;
a microwave antenna movably positioned in the deployable member so as to control a microwave field strength vector in relation to the antenna, the microwave antenna being configured to be coupled to a microwave energy source and deliver microwave energy to a selectable tissue site in the stomach wall while minimizing thermal injury to one of a mucosal or a submucosal layer; and
a cable member coupled to the microwave antenna, the cable member configured to be advancecable within the elongated member, wherein the antenna is configured to produce one of an omnidirectional beam, a pencil-beam, a flat-top flared beam or an asymmetrically flared beam.

62. The apparatus of claim 1, wherein the microwave absorption varies with respect to at least one of a temperature or an emitted microwave power.

63. An apparatus to modify a stomach wall comprising:
an elongated member including at least one lumen;
an inflatable balloon coupled to the elongated member, the inflatable balloon configured to be advanceable and removable from the stomach in a non-deployed state and sized to be positioned in the stomach in a deployed state to engage at least portions of the stomach wall, the inflatable balloon further configured to contain a fluidic media, at least a portion of a inflatable balloon wall configured to be cooled by the fluidic media, at least a portion of the inflatable balloon having a contour in the deployed state approximating at least a portion of a stomach interior, wherein the inflatable balloon is sized to produce a selected post treatment stomach volume;
a microwave antenna movably positioned in the inflatable balloon so as to control a microwave field strength vector in relation to the antenna, the microwave antenna being configured to be coupled to a microwave energy source and deliver microwave energy to a selectable tissue site in the stomach wall while minimizing thermal injury to one of a mucosal or a submucosal layer; and
a cable member coupled to the microwave antenna, the cable member configured to be advancecable within the elongated member.

64. The apparatus of claim 63, wherein the expansion member is sized to produce a selected post treatment stomach volume.

65. The apparatus of claim 63, wherein the inflatable balloon is shaped to produce a selected post treatment stomach shape.

66. An apparatus to modify a stomach wall comprising:

an elongated member including at least one lumen;

a deployable member coupled to the elongated member, the deployable member configured to be advanceable and removable from the stomach in a non-deployed state and sized to be positioned in the stomach in a deployed state to engage at least portions of the stomach wall, the deployable member further configured to contain a fluidic media, at least a portion of a deployable member wall configured to be cooled by the fluidic media, at least a portion of the deployable member having a contour in the deployed state approximating at least a portion of a stomach interior, wherein the deployable member is sized to produce a selected post treatment stomach volume;

a microwave antenna movably positioned in the deployable member so as to control a microwave field strength vector in relation to the antenna, the microwave antenna being configured to be coupled to a microwave energy source and deliver microwave energy to a selectable tissue site in the stomach wall while minimizing thermal injury to one of a mucosal or a submucosal layer; and a cable member coupled to the microwave antenna, the cable member configured to be advancecable within the elongated member.

67. The apparatus of claim 66, wherein the deployable member parameter includes at least one of an expansion member wall thickness, an expansion member shape or an expansion member material.

68. The apparatus of claim 66, wherein the expansion member is configured to at least partial stretch at least a portion of the stomach wall when the expansion member is in the deployed state.

* * * * *